(12) United States Patent
Baesler et al.

(10) Patent No.: US 12,578,300 B2
(45) Date of Patent: Mar. 17, 2026

(54) SENSOR ARRANGEMENT WITH AN ELECTROCHEMICAL SENSOR AND A TEMPERATURE SENSOR AND PROCESS USING SUCH A SENSOR ARRANGEMENT

(71) Applicant: Dräger Safety AG & Co. KGaA, Lübeck (DE)

(72) Inventors: Malte Baesler, Lübeck (DE); Tobias Reier, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 310 days.

(21) Appl. No.: 18/344,978

(22) Filed: Jun. 30, 2023

(65) Prior Publication Data

US 2024/0011939 A1     Jan. 11, 2024

(30) Foreign Application Priority Data

Jul. 6, 2022     (DE) ..................... 10 2022 116 825.5

(51) Int. Cl.
G01N 27/27 (2006.01)
G01K 7/22 (2006.01)
(Continued)

(52) U.S. Cl.
CPC ............. G01N 27/413 (2013.01); G01K 7/22 (2013.01); G01N 27/27 (2013.01); G01N 27/40 (2013.01); *A61B 5/082* (2013.01); *A61B 5/4845* (2013.01)

(58) Field of Classification Search
CPC ...... G01N 27/413; G01N 27/27; G01N 27/40; G01N 27/404; G01N 27/4045; G01K 7/22; A61B 5/082; A61B 5/4845
See application file for complete search history.

(56) References Cited

U.S. PATENT DOCUMENTS 3,518,179 A     6/1970 Bleak et al.
3,815,074 A *   6/1974 Nagata ................... H01C 17/28
29/613
(Continued)

FOREIGN PATENT DOCUMENTS

DE     102017008008 A1     2/2019
DE     102020115804 A1     12/2021
(Continued)

OTHER PUBLICATIONS

Wavelength Electronics article entitled, "Thermistor Basics", Application Note AN-TC11 Rev. A, May 2013, author unknown, downloaded from https://www.teamwavelength.com/download/applicationtechnotes/an-tc11.pdf (Year: 2013).*
(Continued)

*Primary Examiner* — Alexander S Noguerola
(74) *Attorney, Agent, or Firm* — McGlew and Tuttle, P.C.

(57) ABSTRACT

A sensor arrangement (100) and a process analyze a gas for at least one predetermined component and includes an electrochemical sensor (10) with a measuring electrode (20) and a counter electrode (21). An electrolyte (28) is arranged between the electrodes (20, 21). The process is carried out using such a sensor arrangement. A contact segment (7) of an electrically conductive measuring element (6, 7) is in thermal and/or electrical contact with a measurement object (20) (measuring electrode, counter electrode, or electrical contact). A connection segment (6) of the measuring element connects the contact segment to a temperature sensor (9) spatially distanced from the measurement object. The temperature sensor directly or indirectly measures the temperature of the contact segment, particularly the temperature of the connection segment. Depending on this measurement result, the temperature of the measuring electrode and/or the
(Continued)

temperature of the counter electrode is determined and optionally controlled.

14 Claims, 8 Drawing Sheets

(51) Int. Cl.

| | |
|---|---|
| *G01N 27/40* | (2006.01) |
| *G01N 27/404* | (2006.01) |
| *G01N 27/413* | (2006.01) |
| *A61B 5/00* | (2006.01) |
| *A61B 5/08* | (2006.01) |

(56) References Cited

U.S. PATENT DOCUMENTS

| | | | | |
|---|---|---|---|---|
| 3,871,981 | A | * | 3/1975 | Flais ................. G01N 27/4067 |
| | | | | 204/427 |
| 3,966,579 | A | * | 6/1976 | Chang ............... G01N 27/4045 |
| | | | | 429/432 |
| 4,784,728 | A | * | 11/1988 | Capone .............. G01N 27/4067 |
| | | | | 204/427 |
| 11,474,096 | B2 | | 10/2022 | Rekow et al. |
| 2014/0061043 | A1 | | 3/2014 | Stock et al. |
| 2015/0076007 | A1 | | 3/2015 | Compton et al. |
| 2016/0033442 | A1 | * | 2/2016 | Sun ........................ C12Q 1/001 |
| | | | | 204/408 |
| 2016/0245797 | A1 | * | 8/2016 | Ahmad .................. G01N 33/52 |

FOREIGN PATENT DOCUMENTS

| | | | |
|---|---|---|---|
| GB | 1432898 | A | 4/1976 |
| JP | 2021156740 | A | 10/2021 |

OTHER PUBLICATIONS

DwyerOmega online article entitled "Working principle of thermo-couples", author unknown, publication date not indicated so assumed 2025. Downloaded from https://www.dwyeromega.com/en-us/resources/how-thermocouples-work (Year: 2025).*

EPO machine-generated English language translation of JP 2021-156740 A, patent published Oct. 7, 2021 (Year: 2021).*

* cited by examiner

SENSOR ARRANGEMENT WITH AN ELECTROCHEMICAL SENSOR AND A TEMPERATURE SENSOR AND PROCESS USING SUCH A SENSOR ARRANGEMENT

CROSS REFERENCE TO RELATED APPLICATIONS

This application claims the benefit of priority under 35 U.S.C. § 119 of German Application 10 2022 116 825.5, filed Jul. 6, 2022, the entire contents of which are incorporated herein by reference.

TECHNICAL FIELD

The invention relates to a sensor arrangement and a process for analyzing a gas for at least one predetermined gas component, wherein the sensor arrangement comprises an electrochemical sensor having a measuring electrode and a counter electrode, wherein an electrolyte is arranged between these two electrodes, and wherein the process is carried out using such a sensor arrangement.

BACKGROUND

Such electrochemical sensors are used, for example, in alcohol analyzers. Such an analyzer examines the content of breath alcohol, in particular ethanol, in a breath sample exhaled by a subject. The amount of breath alcohol in the breath sample is a measure of the amount of alcohol in the subject's blood.

US 2015/0 076 007 A1 describes an electrochemical sensor with a working electrode (measuring electrode), a counter electrode (return electrode) and an electrolyte between the two electrodes. Different electrical voltages can be applied to the measuring electrode so that different positive potentials of the measuring electrode occur relative to a reference electrode. Two different electrochemical reactions are brought about, namely an oxidation or a reduction of a first chemical substance and an oxidation or reduction of a second chemical substance. A temperature sensor measures a first electrical potential at which the first electrochemical reaction occurs and a second electrical potential at which the second electrochemical reaction occurs, both at the same temperature. From the difference between the two measured electrical potentials, the temperature of the measuring electrode is approximately derived.

SUMMARY

It is an object of the invention to provide a sensor arrangement for analyzing a gas, the sensor arrangement comprising a measuring electrode, a counter electrode and an electrolyte and having a higher reliability than known such sensor arrangements. Furthermore, the invention is based on the task of providing a process for analyzing a gas, wherein the process is carried out using such a sensor arrangement and is intended to have a higher reliability than known processes.

The task is accomplished by a sensor arrangement having features according to the invention and by a process having features according to the invention. Advantageous embodiments of the sensor arrangement according to the invention are, as far as useful, also advantageous embodiments of the process according to the invention and vice versa.

The sensor arrangement according to the invention and the process according to the invention are capable of analyzing a gas for at least one predetermined gas component. The gas is, for example, air and in particular breathing air exhaled by a subject or ambient air. The predetermined gas component is preferably oxidizable and, for example, ethanol, carbon monoxide or methanol.

In one application, the sensor arrangement and the process automatically decide whether the amount and/or concentration (content) of the gas component or at least one gas component in the gas is below or above a predetermined threshold. In another application, the sensor arrangement and the process measure the amount and/or the concentration of the or at least one gas component in the gas at least approximately, optionally the summed concentrations of all predefined gas components.

It is also possible that the sensor arrangement and process measure an amount of the gas component in an amount of a sample of the gas, the amount or volume of the gas sample being known, the measured amount of the component and the known amount of the gas sample being used to derive the sought concentration of the gas component.

The sensor arrangement according to the invention comprises an electrochemical sensor. This electrochemical sensor comprises a measuring electrode, a counter electrode, an electrical contact for the measuring electrode, an electrical contact for the counter electrode, and an electrolyte between the measuring electrode and the counter electrode.

The sensor arrangement is capable of measuring a detection variable of the electrochemical sensor. The measured detection variable is preferably an electrical variable, for example an electrical voltage between the two electrical contacts or the strength of an electrical current flowing through a connection between the two electrical contacts, an electrical charge (amount of current flowing) or an electrical resistance. The detection variable correlates to the presence and/or amount and/or concentration of the or at least one gas component in the gas. For example, the gas component causes a chemical reaction in or at the electrochemical sensor, and the chemical reaction affects the detection variable, particularly the electrical voltage or the strength of an electrical current. The measured detection variable is therefore an indicator of the amount of the gas component in a given amount of the gas and/or of the concentration of the gas component in the gas. The detection variable is usually larger or smaller the larger the amount or concentration of the gas component in the gas that is sought.

The sensor arrangement further comprises a temperature sensor unit which is able to determine at least approximately the current temperature of the measuring electrode and/or the current temperature of the counter electrode. The temperature sensor unit comprises an electrically conductive measuring element and a temperature sensor. The measuring element comprises a contact segment and a connection segment. These two segments are electrically and/or thermally conductively connected to each other.

The contact segment is in surface contact (planar contact—areal contact) with a measurement object (target) belonging to the electrochemical sensor. Thanks to this two-dimensional (flat) contact, thermal contact is established between the contact segment and the measurement object. Thanks to the thermal contact, the contact segment and the measurement object ideally have the same temperature. The term "measurement object" of the sensor arrangement is understood to mean the measuring electrode, the counter electrode, the electrical contact for the measuring electrode or the electrical contact for the counter electrode. With other words: The contact segment is in a surface contact with the measuring electrode, the counter electrode, the electrical contact for the measuring electrode or the electrical contact for the counter electrode. It is also possible that the same contact segment is in planar contact with two different measurement objects or that two different contact segments are in planar contact with one measurement object each, whereby the same connection segment or two different connection segments is/are connected to the two contact segments.

The connection segment electrically and/or thermally connects the contact segment or a contact segment to the temperature sensor. Preferably both the connection segment and the temperature sensor are spatially spaced from both electrodes as well as from both electrical contacts for these electrodes.

The temperature sensor is able to measure at a measuring position a variable that correlates with the temperature of the contact segment at the measuring position. The measuring position is spaced apart from both electrodes and from both electrical contacts. This measured variable is in particular the temperature of the connection segment or a variable that correlates with the temperature of the connection segment. It is possible that the measured variable is the temperature of the connection segment at the measuring point. The measuring position can comprise a single measuring point or two single measuring points, in particular two measuring points between which an electrical voltage occurs which is measured.

The temperature sensor unit is able to determine the current temperature of the measuring electrode and/or the current temperature of the counter electrode depending on the measured variable that correlates with the temperature of the contact segment and which was measured at the measuring position.

The process according to the invention is carried out using such a sensor arrangement and comprises the following steps:

The detection variable of the electrochemical sensor is measured. This detection variable correlates with the sought presence and/or concentration of the or at least one gas component in the gas.

The temperature sensor measures at the measuring position the variable that correlates with the temperature of the contact segment. In particular, the temperature sensor measures a variable that correlates with the temperature of the connection segment.

Depending on the variable correlating with the temperature of the contact segment, an indicator of the temperature of the measuring electrode and/or the temperature of the counter electrode is determined (the temperature is determined at least approximately).

According to the invention, a detection variable is measured, whereby this detection variable depends on the amount and/or concentration of the component in the gas. However, the detection variable often depends not only on the amount and/or concentration of the component, but additionally on the temperature of the measuring electrode and/or on the temperature of the counter electrode. This electrode temperature is usually influenced by ambient conditions, in particular by the ambient temperature and/or the temperature in a measuring chamber of the sensor arrangement and, to a lesser extent, by the humidity and temperature of the gas to be analyzed.

In many cases, the lower the temperature of the measuring electrode, the longer it takes to analyze the gas. In some cases, a long analysis time results in relatively high measurement noise. In particular, when the ambient temperature is relatively low, moisture may condense in a fluid-guiding unit, such as a hose, with this fluid-guiding unit leading to the electrochemical sensor. The condensed moisture can change the chemical composition of the gas and therefore distort a measurement result of the electrochemical sensor. Furthermore, in some cases, when the measuring electrode has a low temperature, moisture may condense on the measuring electrode, which may also falsify a measurement result. In addition different temperatures may occur at different positions within the electrochemical sensor at one time point. In particular, for capturing and at least partially compensating these dynamical effects, it is desired to know the current temperature of at least one electrode of the electrochemical sensor with sufficient reliability.

The temperature sensor unit is able to determine at least approximately the current temperature of the measuring electrode and/or the temperature of the counter electrode. The information as to the electrode temperature makes it possible in many cases to automatically compensate by calculation the influence of the electrode temperature on the measurement result to a certain degree and/or to control the electrode temperature by closed-loop control.

According to the invention, the temperature sensor is able to measure at the measuring position a variable that correlates with the temperature of the contact segment. Thanks to the two-dimensional contact and the resulting thermal contact, the contact segment has approximately the same temperature as the measurement object. "Approximately the same temperature" means that possible temperature differences are so small that they can be neglected for applications of the invention, and/or are smaller than a given tolerance.

The measurement object can be the electrode or one electrode wherein the temperature of this electrode is to be measured. It is also possible that the measuring object is the electrical contact for this electrode. As a rule, the electrical contact for an electrode has approximately the same temperature as the electrode being contacted. Therefore, the temperature of the electrode can be measured with sufficient reliability if the contact segment contacts the electrical contact of the electrode and is arranged in a distance to the electrode itself. In some applications it is easier to implement an areal contact between the contact segment and the electrical contact than with the electrode itself.

In some cases it is possible to apply a given computing procedure onto the measured variable for deriving the temperature of the electrode. This computing procedure is determined by the construction of the sensor arrangement. Therefore, no additional sensor is required for applying the computing procedure.

According to the invention, the temperature sensor is capable of measuring, at the measuring position, a variable (correlating variable) that correlates with the temperature of the contact segment. The correlating variable is, for example, the electrical resistance or a measurable variable that correlates with the electrical resistance. The measuring position can be in or at the connection segment. In this case the temperature sensor is capable of measuring a variable which correlates with the temperature of the connection segment.

According to the invention the variable which correlates with the contact segment temperature is measured at the measuring position wherein the measuring position is spatially distanced (spaced) from both electrodes and both electrical contacts. Thanks to this feature it is not necessary to measure the temperature at a measuring position which is positioned at or on or in the measurement object or the contact segment. In contrast the connection segment contributes to bridging the distance between the measuring object and the contact segment on the one hand and the measuring position on the other hand.

Thanks to the invention it is possible to measure the temperature of at least one electrode while the sensor arrangement and thereby an analyzer which comprises the sensor arrangement is productively used. Thanks to the invention it is not necessary to transfer the sensor arrangement into a specific mode for measuring the electrode temperature. In addition it is thanks to the invention not necessary to add a chemical substance to the sensor arrangement only for the sake of measuring the electrode temperature. In many cases measuring the electrode temperature only requires little time. This feature often makes it possible to control the electrode temperature quickly to a preset value.

According to the invention the temperature sensor is capable of measuring at the measuring position the variable which correlates with the contact segment temperature. This measuring position is distanced from both electrodes and from both electrical contacts. Preferably the entire sensor arrangement or at least the electrochemical sensor is arranged in the interior of a housing. The measuring position is preferably also arranged in the interior of this housing. This feature reduces the risk that the housing falsifies a measurement result.

According to the invention the temperature sensor unit is capable of measuring the temperature of the measuring electrode and/or the temperature of the counter electrode and optionally the respective temperature of both electrodes. In many cases the electrochemical sensor further comprises a reference electrode and an electrical contact for the reference electrode. In general, the electrical potential of the reference electrode is kept at a constant value. In many cases a gas sample to be investigated does not reach the reference electrode. In many cases the detection variable further depends on the temperature of the reference electrode.

In one embodiment the temperature sensor unit is further capable of measuring the temperature of the reference electrode. The contact segment of the measuring element or a contact segment of a further measuring element is in planar contact with the reference electrode or with the electrical contact for the reference electrode such that thermal contact is established. The temperature sensor according to the invention or a further temperature sensor is capable of measuring a variable which correlates with the temperature of the contact segment which contracts the reference electrode or the electrical contact for the reference electrode. In many cases this embodiment makes it possible to control the temperature of the reference electrode and in particular to keep this reference electrode temperature constant.

In one realization, the so-called Seebeck effect (thermo-electric effect) is exploited to measure the temperature of the electrode. This Seebeck effect is first explained in general terms with reference to FIG. 1.

The temperature of an object at a point P1 is to be measured. An electrical conductor A is electrically connected to an electrical conductor B at point P1. The temperatures of the two conductors A and B in P1 and the sought object temperature in P1 coincide sufficiently exactly. The two conductors A and B have two different Seebeck coefficients k(A) and k(B). The property "Seebeck coefficient" is also called "thermal capacity" or "thermoelectric sensitivity" and is a material-specific constant. The unit is preferably micro-volts per Kelvin.

According to the Seebeck effect, a so-called thermo-voltage U(Th) occurs. This thermo-voltage U(Th) occurs between a point P3 on conductor A and a point P2 on conductor B, with a distance occurring between P1 and P2, between P1 and P3, and between P2 and P3, respectively. For example, conductor A extends from P1 to P3 and conductor B extends from P1 to P2. The temperature of conductor A in P3 and the temperature of conductor B in P2 are assumed to coincide sufficiently. The thermo-voltage U(Th) depends on the two Seebeck coefficients k(A) and k(B), usually the difference k(A)–k(B), and also on the temperature Temp(P1) in P1 and on the temperature Temp (P3) of conductor A in P3, which coincides with the temperature Temp(P2) of conductor B in P2. The two Seebeck coefficients k(A) and k(B) are known by design, and the thermal voltage U(Th) and the temperature Temp(P3) of conductor A in P3 or the temperature Temp(P2) of conductor B in P2 are measured. Then the sought Temp(P1) can be derived. In many cases it is valid with sufficient accuracy:

$$U(Th)=[k(A)-k(B)]*[\text{Temp}(P1)-\text{Temp}(P2)]=[k(A)-k(B)]*[\text{Temp}(P1)-\text{Temp}(P3)].$$

In this calculation Temp(P1) is the only unknown.

According to the preferred embodiment of the invention, the Seebeck effect is exploited as follows: The area in which the contact segment is in planar contact with the measurement object acts as the or comprises the point P1. At least at point P1, the contact segment is also electrically connected to the measurement object. A segment of the electrical contact for an electrode belongs to the electrical conductor A. The electrically conductive connection segment acts as the electrical conductor B. The two points P2 and P3 each are located at a spatially distant reference measuring position, for example on a circuit board to which the two conductors A and B are connected. Preferably, the two points P2 and P3 serve as the spatially distanced measuring position. The electrically conductive measuring element or at least the connection segment has a different Seebeck coefficient than the electrical conductor A. As a rule, it is justified to assume that the connection segment has the same Seebeck coefficient throughout its length and that the electrical conductor A also has the same Seebeck coefficient throughout its length. The two Seebeck coefficients are known from the design of the sensor arrangement or can be determined empirically in advance.

The temperature sensor unit includes a voltage sensor in addition to the temperature sensor. The voltage sensor is spatially spaced from both electrodes and is capable of measuring an indicator of the thermal voltage U(Th) between points P2 and P3. The thermal voltage U(Th) occurs between the connection segment on the one side and the measurement object or the electrical contact for the measurement object on the other side. According to this embodiment, the temperature sensor is capable of measuring the temperature of the connection segment or a variable that correlates with the temperature of the connection segment. The temperature sensor unit uses the temperature of the connection segment as the temperature at point P2 and/or at point P3 or derives the temperature at point P2 or at point P3 from the temperature of the connection segment. In many cases, the temperatures at points P2 and P3 do not differ significantly. The temperature sensor unit derives the temperature at point P1 from the measured thermal voltage, the measured temperature at point P2 and/or P3 and the two Seebeck coefficients, preferably the difference
       between the two Seebeck coefficients.

This embodiment eliminates the need to directly measure the temperature of the contact segment or a variable that correlates with the temperature of the contact segment. Further, it is possible, but not necessary, for the contact segment to be in good thermal contact with the connection segment. Rather, according to this embodiment, a temperature is measured at a spatially remote position, namely at point P2 or P3. In many cases, much more space is available for a temperature sensor at point P2 or at point P3 than at point P1. In addition, the temperature or a variable correlating with the temperature can be measured with greater reliability and/or more quickly at point P2 or at point P3 than at point P1. In many cases, this embodiment also eliminates the need to electrically insulate the electrically conductive measuring element or at least the contact segment from the measurement object. Such electrical insulation requires space and may leak, thus allowing electrical contact in an undesirable manner. An undesired electrical contact may falsify a measurement result of the sensor arrangement.

In the following, an implementation of the embodiment with the Seebeck effect is described. According to this implementation, the measurement object is the measuring electrode or the counter electrode. The contact segment contacts the electrode acting as the measurement object. The connection segment has a different Seebeck coefficient than the electrical contact of the electrode serving as the measurement object. The voltage sensor is able to measure an indicator for the following thermal voltage: for the thermal voltage which occurs between the connection segment and the electrical contact of the measurement object.

According to this further development, the contact segment of the measuring element contacts the electrode thermally and electrically at point P1. In many cases the temperature of this electrode can be derived better than if the contact segment would contact the electrical contact of the electrode and not the electrode itself. The electrical contact of the electrode, which is present anyway, is additionally used to measure the thermal voltage.

According to the embodiment exploiting the Seebeck effect, the temperature sensor is capable of measuring a variable correlating with the temperature of the connection segment. In one realization form, the measuring electrode or the counter electrode is used as the measurement object. According to this realization form, as the variable that correlates with the temperature of the connection segment, the temperature of the electrical contact of that electrode that acts as the measurement object is measured. Again, the thermal voltage between the measuring element and the electrical contact is measured. In some cases, this advanced formation increases the reliability with which, using the Seebeck effect, the sought temperature of the electrode is determined.

According to the invention, the contact segment is in thermal contact with the measurement object. The temperature sensor is preferably capable of measuring a variable that correlates with the temperature of the contact segment. In one embodiment, this variable is the temperature of the contact segment or a variable that correlates with the temperature of the contact segment. In some cases, the temperature of the connection segment does not deviate in a relevant way from the temperature of the measurement object. In other cases the temperature of the contact segment and thereby the temperature of the electrode can be derived from the temperature of the connection segment, e.g. by exploiting the Seebeck effect as just described.

According to an alternative embodiment of the invention, in order to prevent the contact segment from falsifying a measurement result of the electrochemical sensor, the contact segment is electrically insulated from the measurement object, for example by an insulating sheath around the contact segment. The connection segment is spatially distanced from both electrodes and from both electrical contacts and therefore does not necessarily need to be electrically insulated. Thanks to the thermal contact between the measurement object and the contact segment, the contact segment has the same temperature as the measurement object with sufficient accuracy, despite of the electrical insulation. Particularly preferably, the measurement object is the measuring electrode or the counter electrode. The temperature sensor is capable of measuring at the measuring position the variable that correlates with the temperature of the contact segment. In one implementation the measuring position is at the connection segment.

The alternative embodiment just described eliminates the need to provide two electrically conductive components with different Seebeck coefficients. In addition, a voltage sensor is not necessarily required. The temperature sensor is spatially distanced from the measurement object and from the contact segment.

In one implementation, a measure of the electrical resistance of the contact segment is measured as the variable that correlates with the temperature of the contact segment. For example, at least temporarily an electrical circuit is established wherein this electrical circuit comprises the contact segment. The electrical voltage applied to the connection segment and the magnitude of the current flowing through the connection segment are measured. As is well known, the electrical resistance of an electrically conductive element correlates with its temperature. Because the electrical resistance of the contact segment is measured, in many cases it is not necessary to electrically contact the contact segment or the measurement object to measure the electrical resistance. This reduces the risk that the measurement of the electrical resistance will falsify a measurement result of the electrochemical sensor.

In a preferred embodiment, the sensor arrangement according to the invention additionally comprises a controllable heater. The controlled and thus activated heating is able to heat the measuring electrode and/or the counter electrode.

According to the embodiment with the heater, a signal processing controller of the sensor arrangement is able to control the actual temperature of the measuring electrode and/or the actual temperature of the counter electrode. The control gain in this control is to keep the actual electrode temperature within a predetermined temperature range. In order to increase the actual electrode temperature and thereby reduce the control deviation, the control unit is able to control the heater and thereby activate it. In order to achieve the control gain and to control the heater for this purpose, the control unit uses a signal from the temperature sensor unit. The control unit can also deactivate the heater.

An advantageous embodiment of the process according to the invention is carried out using a controllable heater and a signal-processing controller and comprises the additional step of automatically controlling the actual temperature of the measuring electrode and/or that of the counter electrode. The control gain in this control (closed-loop control) is that the actual temperature of the electrode remains within a predetermined temperature range. For the control, the control unit uses a signal from the temperature sensor unit.

Then, when the measured actual temperature is below the temperature range, the control unit activates the heater. The activated heating heats the electrode. Later, namely when the actual temperature is again within the temperature range, the control unit deactivates the heating again.

The preferred embodiment that the electrode temperature is controlled automatically has in particular the advantages described below.

If the temperature of the measuring electrode is very high, there is a greater risk that the measuring electrode or another component of the sensor arrangement will be thermally damaged, that some of the electrolyte will evaporate and/or that deposits will form on the measuring electrode. In addition, in some cases a lot of electrical energy is consumed, which is particularly disadvantageous if the sensor arrangement cannot be permanently connected to a stationary voltage supply network. However, an analyzer device with the sensor arrangement according to the invention may comprise its own voltage supply unit. The analysis device can be a portable device.

Thanks to the control according to the invention, the temperature of the measuring electrode is kept within the specified temperature range. Both the disadvantages of a very low and the disadvantages of a very high temperature are avoided. Compared to an embodiment without a temperature control, this reduces the time required to analyze the gas. In addition, to a certain extent the influence of ambient conditions on the analysis result is compensated by calculation. It is not necessary to measure an indicator of an ambient condition, such as ambient temperature.

In one embodiment, the temperature of the measuring electrode is controlled directly; in another embodiment, the temperature of the counter electrode, which influences the temperature of the measuring electrode, is controlled. Both too low and too high a temperature of the measuring electrode are prevented. It is also possible that both the temperature of the measuring electrode and the temperature of the counter electrode are controlled. Preferably, therefore, the heating is switched on only as long as necessary. It is also possible to control the temperature of the optional reference electrode.

According to the invention, the contact segment is in thermal contact with the measurement object. In one embodiment, the measurement object is the measuring electrode and/or is the counter electrode. Even when the measurement object is an electrical contact, the measurement object generally has approximately the same temperature as the measuring electrode and the counter electrode. On the one hand, the measuring position is spatially distanced from both electrodes and from both electrical contacts. On the other hand the measuring position is preferably sufficiently close to at least one electrode and in particular in the interior of a housing. If the measuring position were further away from the electrode, there could be a greater time delay between a change in temperature and a corresponding response from the control unit. This danger is particularly present if the sensor arrangement is inside a housing and the measuring position is located on the outside of the housing or even at a distance from the housing. In addition, if there is a large distance between the measuring position and the electrode, there is a greater risk that an interference variable in the form of another heat source or cold source will falsify the temperature measurement.

Thanks, in particular to the feature with the contact segment, the temperature sensor unit provides a signal for the current temperature of the measurement object, whereby this signal quickly follows temperature changes of the measurement object. The control unit is therefore able to react quickly to a temperature change of the measurement object and thus of an electrode. Thanks to this rapid response, in many cases it is achieved that the actual electrode temperature is outside the specified temperature range only for very short periods of time.

In one embodiment, the temperature sensor is capable of measuring both the actual temperature of the measuring electrode and the actual temperature of the counter electrode. In an advanced embodiment with the heater, one component of the heater is able to heat the measuring electrode, another component is able to heat the counter electrode. These two components can preferably be controlled independently of each other. Depending on the measured actual temperature of the measuring electrode, the control unit controls the component for heating the measuring electrode. Depending on the actual temperature of the counter electrode, the control unit controls the component for heating the counter electrode. It is possible that the same desired temperature range is specified for the measuring electrode and for the counter electrode. It is also possible that different temperature ranges are specified.

In one implementation form of the embodiment with the heater, the heater comprises a controllable radiation source. The radiation source is capable of emitting electromagnetic radiation, in particular infrared radiation, in the direction of the measuring electrode and/or the counter electrode. The control unit is able to cause the intensity and/or the energy of the radiation emitted by the radiation source to be adjusted to a value calculated by the control unit. To calculate this value, the control device uses a signal from the temperature sensor unit.

According to the invention, the contact segment of the measuring unit is in thermal contact with the measurement object. According to the just described embodiment, a heater is able to heat the measuring electrode and/or the counter electrode. In one embodiment, the measurement object is also the heated electrode. The heater comprises an electrically conductive heating element. This electrical heating element comprises the contact segment and/or provides the contact segment. This contact segment is in thermal contact with the object to be measured, in this case with the heated electrode. The contact segment is preferably electrically insulated from the heated electrode in order to reduce the risk of a measurement result of the electrochemical sensor being falsified by an electrical contact.

According to this embodiment, the electrically conductive heating element thus has two functions: first, the temperature sensor measures a variable that correlates to the current temperature of the heating element, and the temperature sensor unit derives the temperature of the electrode from the measured variable. The knowledge of the heating element temperature is preferably used to control the heating by closed-loop control or by open-loop control. On the other hand, the same heating element heats the electrode. The embodiment thus eliminates the need to provide a contact segment and additionally a spatially distanced heating element.

According to this embodiment, a variable is measured that correlates with the temperature of the contact segment. In one embodiment, the sensor unit measures an indicator of the electrical resistance of the electrically conductive heating element. As is known, for an electrically conductive element, the electrical resistance correlates with the temperature of the element.

According to a preferred form of implementation of the embodiment with the heater, the control unit calculates a setpoint value for the electrical voltage to be applied to the heater. This value for the electrical voltage applied determines the temperature that the heater delivers to the electrode. To calculate the setpoint for the electrical voltage, the control unit uses a signal from the temperature sensor unit. The control unit controls the heater with the aim of ensuring that the electrical voltage actually applied to the heater is equal to the setpoint.

Preferably, the control unit controls the heater and then activates the heater when the measured actual temperature of the measuring electrode and/or the counter electrode is below the lower limit of the predetermined temperature range. In one embodiment, unilateral control of the actual electrode temperature is sufficient because the actual electrode temperature is not greater, or not greater to a significant degree, than the upper bound of the temperature range. This is particularly the case when the electrode temperature is less than or not significantly greater than the ambient temperature. Furthermore, in many cases the goal of avoiding too low a temperature is more important than the goal of avoiding too high a temperature, because too low a temperature often affects the sensitivity and reliability of the sensor arrangement more than too high a temperature.

In one further variation of this embodiment, a one-sided control is performed, i.e. only heated or not heated. In another variation of this embodiment, the control unit is additionally able to control a cooling, i.e. a cooling element (providing a cooling system), of the sensor arrangement. If the measured actual temperature is above the predetermined temperature range, the control unit activates the cooling. Later, namely when the actual temperature is again within the temperature range, the control unit deactivates the cooling.

In one embodiment, the sensor arrangement thus additionally comprises a controllable cooling system. The cooling system is able to cool the measuring electrode and/or the counter electrode. The control unit controls the cooling system and thus activates the cooling system when the actual temperature is above the specified temperature range. The control unit can also deactivate the cooling system again.

In one embodiment, the sensor arrangement according to the invention belongs to an analyzer, preferably to a portable analyzer. In one application of the invention, the gas that the sensor arrangement is capable of analyzing is a portion of a breath sample that a subject inputs into a mouthpiece or other input unit of the analyzer. The gas component for which the gas is to be analyzed is breath alcohol, in particular ethanol, or other substance that may be present in a subject's exhaled breath and that is detectable. In a further variation of this embodiment, the sensor arrangement measures the concentration of breath alcohol in the breath sample and derives from this breath alcohol concentration the level of alcohol in the blood of the subject. Preferably, the analyzer outputs the alcohol content in a form that can be perceived by a human.

In the following, the invention is described with embodiment examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
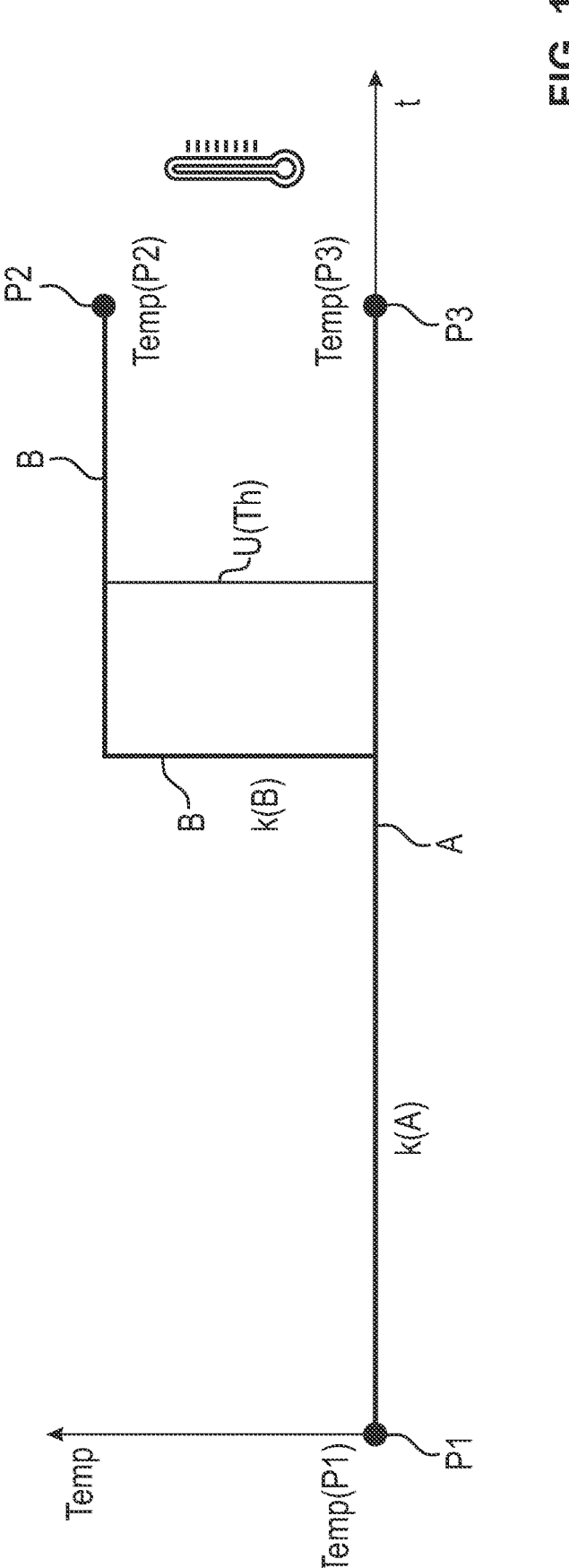
FIG. 1 schematically illustrates the Seebeck effect.

Referring to the drawings, in the embodiment, the sensor arrangement according to the invention is a component of an analyzer, whereby the rest of the analyzer is not shown in the figures. The analyzer with the sensor arrangement is used for analyzing a breath sample of a subject for a predetermined substance, in particular for breath alcohol. In the case of breath alcohol as the substance, in one application the subject is to be analyzed to determine whether or not alcohol is present in his blood above a predetermined detection limit. In another application, the level of alcohol in his blood is to be measured. In one embodiment, the subject may hold the analyzer in one hand. Preferably, the analyzer comprises its own power supply unit.

The subject enters a breath sample into a mouthpiece of the analyzer. If the subject has consumed a beverage or food containing a relevant amount of alcohol, the breath sample supplied contains breath alcohol, in particular gaseous ethanol. In the following, the term "breath alcohol" is used for a possible gaseous substance for which the analyzer with the sensor arrangement according to the invention is to analyze a breath sample, i.e. for the specified gas component.

A part of the delivered breath sample flows into a measuring chamber of the analyzer. This part is referred to below as the "measuring chamber sample". An electrochemical sensor in or on the measuring chamber measures the content or amount of breath alcohol or of another specified substance in this measuring chamber sample. The following description refers to breath alcohol as the substance. In particular, the invention can also be applied to another substance that may be present in the exhaled air of a subject or even in the ambient air.

The electrochemical sensor is able to generate a signal that correlates with the concentration of breath alcohol in the measuring chamber sample that is in the measuring chamber.

Various suitable electrochemical sensors are known from the prior art.

The analyzer derives the concentration of breath alcohol in the input breath sample from the amount or concentration of breath alcohol in the measuring chamber sample and the volume of the measuring chamber sample. For example, the volume of the measuring chamber sample is derived as a function of the volume of the measuring chamber, which is known by the design of the analyzer, and/or a measured and integrated volume flow into the measuring chamber. The analyzer or a spatially remote evaluation unit derives the level of alcohol in the subject's blood from the breath alcohol concentration or the amount of breath alcohol in the breath sample. Of course, the analysis can lead to the result that no alcohol is present in the subject's blood above a detection limit.

As the breath sample passes through the mouthpiece, air first flows from the mouth, then air from the upper respiratory tract, and then air from the subject's lungs flows through the mouthpiece. To determine if the subject's blood contains alcohol, a gas from that portion of the breath sample that originates from the lungs must be tested. Ideally, only gas originating from the subject's lungs flows into the measuring chamber, and the measuring chamber sample contains only air from the lungs. The remaining part of the breath sample flows out of openings in the mouthpiece without reaching the measuring chamber. A mouthpiece with such openings is described, for example, in DE 10 2017 008 008 A1 (corresponding U.S. Pat. No. 11,474,096 B2 is hereby incorporated by reference).

In one embodiment, the analyzer comprises a pump or other fluid delivery unit. This fluid delivery unit is turned on after the subject has begun to introduce the breath sample into the mouthpiece. Ideally, the pump draws in that portion of the breath sample that originates from the subject's lungs. Preferably, the fluid delivery unit flushes out the measuring chamber again after the electrochemical sensor has analyzed the measuring chamber sample. This allows the same analyzer to be used for multiple breath samples in rapid succession. It is also possible for the measuring chamber sample to flow into the measuring chamber by diffusion without using a fluid delivery unit.

Figure 2:
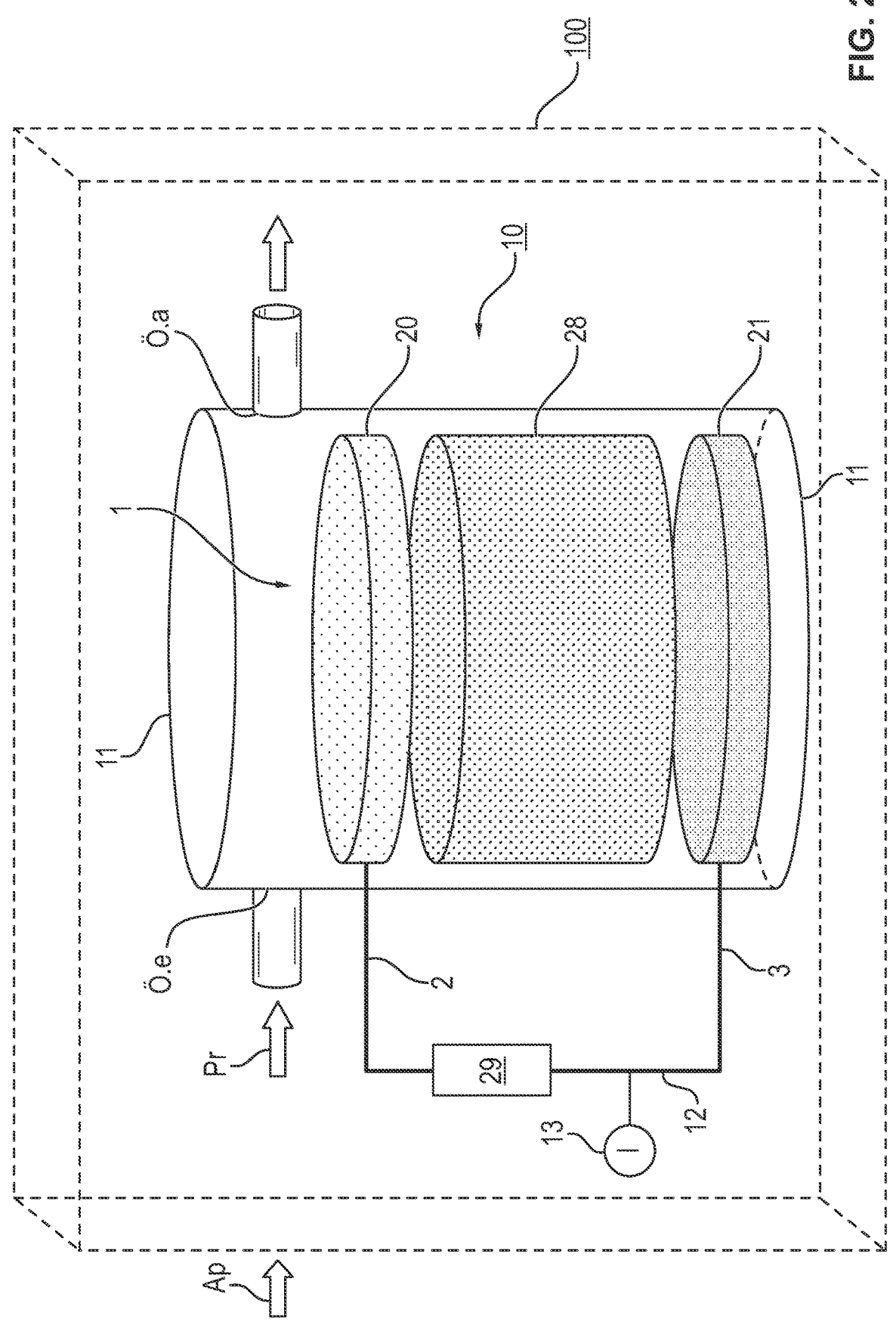
FIG. 2 is a schematic view showing a sensor assembly and illustrating the mode of operation of an electrochemical sensor that is a part of the sensor assembly.

The analyzer of the embodiment comprises a sensor assembly 100 having an electrochemical sensor 10. FIG. 2 schematically shows the mode of operation of the electrochemical sensor 10. The representation of FIG. 2 is not necessarily true to scale. In one embodiment, the analyzer according to the invention comprises such a sensor arrangement 100 and receives a breath sample Ap.

The electrochemical sensor 10 comprises a housing 11 enclosing a measuring chamber 1. A measuring chamber sample Pr to be examined flows through an inlet-side opening Ö.e into the interior of the housing 11 and there to the measuring chamber 1, for example by diffusion or by the measuring chamber sample Pr being actively sucked through the opening Ö.e into the interior of the housing 11. The measuring chamber sample Pr flows back out of the measuring chamber 1 and then out of the housing 11 through an outlet side opening Ö.a. Therefore, the same sensor 10 can successively examine several measuring chamber samples Pr.

The electrochemical sensor 10 comprises
a measuring electrode 20, which is electrically contacted by a contacting wire 2,
a counter electrode 21, which is electrically contacted by a contact wire 3,
an electrolyte 28 between the two electrodes 20 and 21, a connecting wire 12 electrically connecting the two contacting wires 2 and 3 and comprising an electrical measuring resistor 29, and
a current (amperage) sensor 13 that measures the intensity of the current flowing through the connecting wire 12.

Such an electrochemical sensor 10 is also referred to hereinafter as a membrane electrode electrolyte unit (MEEE).

The electrolyte 28 is an electrically conductive medium, for example sulfuric acid diluted with water or phosphoric acid or perchloric acid. Ions can move in the electrolyte 28. Preferably, a membrane provides the electrolyte 28. The electrolyte 28 provides an ionically conductive connection between the measuring electrode 20 and the counter electrode 21 but prevents a short circuit between the two electrodes 20 and 21.

The sensor 10 is configured such that the measuring chamber sample Pr reaches only the measuring electrode 20, but not the counter electrode 21. In the example shown, the measuring electrode 20 is located on a wall of the measuring chamber 1, and the housing 11 and the electrolyte 28 prevent a relevant amount of the measuring chamber sample Pr from reaching the counter electrode 21.

The two contact wires 2 and 3 are electrically conductive and made of a material which is not chemically attacked by the electrolyte 28, for example platinum or gold. The electrodes 20 and 21 are also made of a chemically resistant material, for example, also made from platinum or gold. In many cases, the chemically resistant material additionally acts as a catalyst for a chemical reaction caused and used for measurement.

In one embodiment, the electrochemical sensor 10 operates on the principle of a fuel cell. The chemical reaction used for measurement includes the step of oxidizing the breath alcohol in the measuring chamber sample Pr in the measuring chamber 1. Ideally, the entire amount of breath alcohol in the measuring chamber sample Pr is oxidized. As a result of the chemical reaction, an electrical voltage occurs between the measuring electrode 20 and the counter electrode 21, and therefore an electrical current flows through the connecting wire 12. The current (amperage) sensor 13 measures the current I and therefore a measure of the electrical charge, i.e. the total charge transferred by the electrical current flowing through the connecting wire 12 (principle of coulometry). As is well known, the electric charge is the integral of the current (amperage) over time. For a given volume of measuring chamber sample Pr in measuring chamber 1, the more breath alcohol the measuring chamber sample Pr contains before oxidation, the higher the measured electric charge. The measured electric charge is therefore a measure of the amount of breath alcohol in the measuring chamber sample Pr and thus of the breath alcohol content in the breath sample A and of the content of alcohol in the subject's blood. The electric charge is thus the detection variable of the embodiment.

The electrochemical sensor 10 provides an electrical signal that is a measure of the amount of breath alcohol in the measuring chamber sample Pr. However, this signal depends not only on the amount or concentration of breath alcohol in the measuring chamber sample Pr, but is also influenced by the temperature of the two electrodes 20 and 21. In order for the sensor 10 to provide a reliable measurement result, in the embodiment example the temperature of the electrodes 20, 21 is controlled with the control gain that the temperature should remain within a predetermined temperature range. A special case is that a constant target temperature is specified and the temperature of the electrodes 20, 21 is controlled with the control gain that the temperature should be constantly equal to this target temperature. A closed-loop control and not only an open-loop control of the electrode temperature is carried out, because the temperature of the electrodes 20, 21 is particularly influenced by the ambient temperature. It is possible, but not necessary thanks to the closed-loop control, to measure the ambient temperature directly.

Preferably, the predetermined temperature range comprises the typical temperature of a breath sample emitted by a human. This average temperature is between 32° C. and 38° C., particularly preferably equal to 35° C. For the following reasons, the temperature range should not be too low:

The higher the temperature of the electrodes 20, 21, the faster the sensor 10 provides a result. This is because the higher the temperature, the faster the electrochemical reaction takes place. A low time requirement to provide the result is especially important if the same analyzer is to be used successively to test several breath samples for breath alcohol.

The more time the analysis of the measuring chamber sample Pr requires, the greater the measurement noise in many cases. One possible cause for the measurement noise is that the electric charge is determined numerically by an inevitably only approximate integration over several measured values of the current (amperage). As a rule, the longer the period over which numerical integration is performed, the greater the measurement noise. One reason is that a calculated zero point (reference point) is used for the analysis. Calculating the zero point is inevitably connected with errors period these errors have a stronger effect the longer the time period is.

If the temperature of the electrodes 20, 21 is too low, there is a risk that moisture will condense in the measuring chamber 1 or on a fluid guide unit leading to the measuring chamber 1. Breath alcohol may condense and/or dissolve in the condensed moisture. The electrochemical sensor 10 may then measure a content of alcohol that is too low. In addition, condensed moisture could enter the measuring chamber 1 as a component of the measuring chamber sample Pr. This can also lead to an incorrect measurement result.

A very high temperature of the electrodes 20, 21, on the other hand, can damage the sensor 10. In particular, a housing 11 made of plastic may be damaged, or part of the electrolyte 28 may evaporate, or harmful substances may be deposited on an electrode 20, 21. In addition, a high temperature requires more electrical energy than necessary. Especially if the analyzer is not connected to a stationary voltage supply network but has its own voltage supply unit, the electrode temperature should therefore not be higher than necessary.

For the following additional reasons, the temperature of electrodes 20, 21 should not differ too much from measurement to measurement:

For a given amount of breath alcohol in the measuring chamber sample Pr, the lower the temperature in the measuring chamber 1, the lower the measured value, in particular the measure of electrical charge. Thus, the lower the temperature in the measuring chamber 1, the less sensitive the sensor 10. This temperature dependence makes adjustment and calibration of the sensor 10 difficult.

The measure for the electric charge is usually measured by measuring an indicator for the current (amperage) at several sampling times and integrating the measured values for the current (amperage). This procedure inevitably results in measurement noise. The influence of this measurement noise is greater the longer the measurement takes, i.e., the more time elapses to oxidize the breath alcohol in measuring chamber 1. Therefore, the lower the temperature in measuring chamber 1, the greater the influence of the measurement noise.

In one embodiment, the temperature of the measuring electrode 20 is controlled, and any temperature difference between the temperatures of the two electrodes 20, 21 is neglected. An alternative embodiment is described below.

In the figures the entire sensor arrangement is denoted by the reference numeral 100. The sensor arrangement 100 comprises an electrochemical sensor 10, which can be configured as described with reference to FIG. 2.

Figure 3:
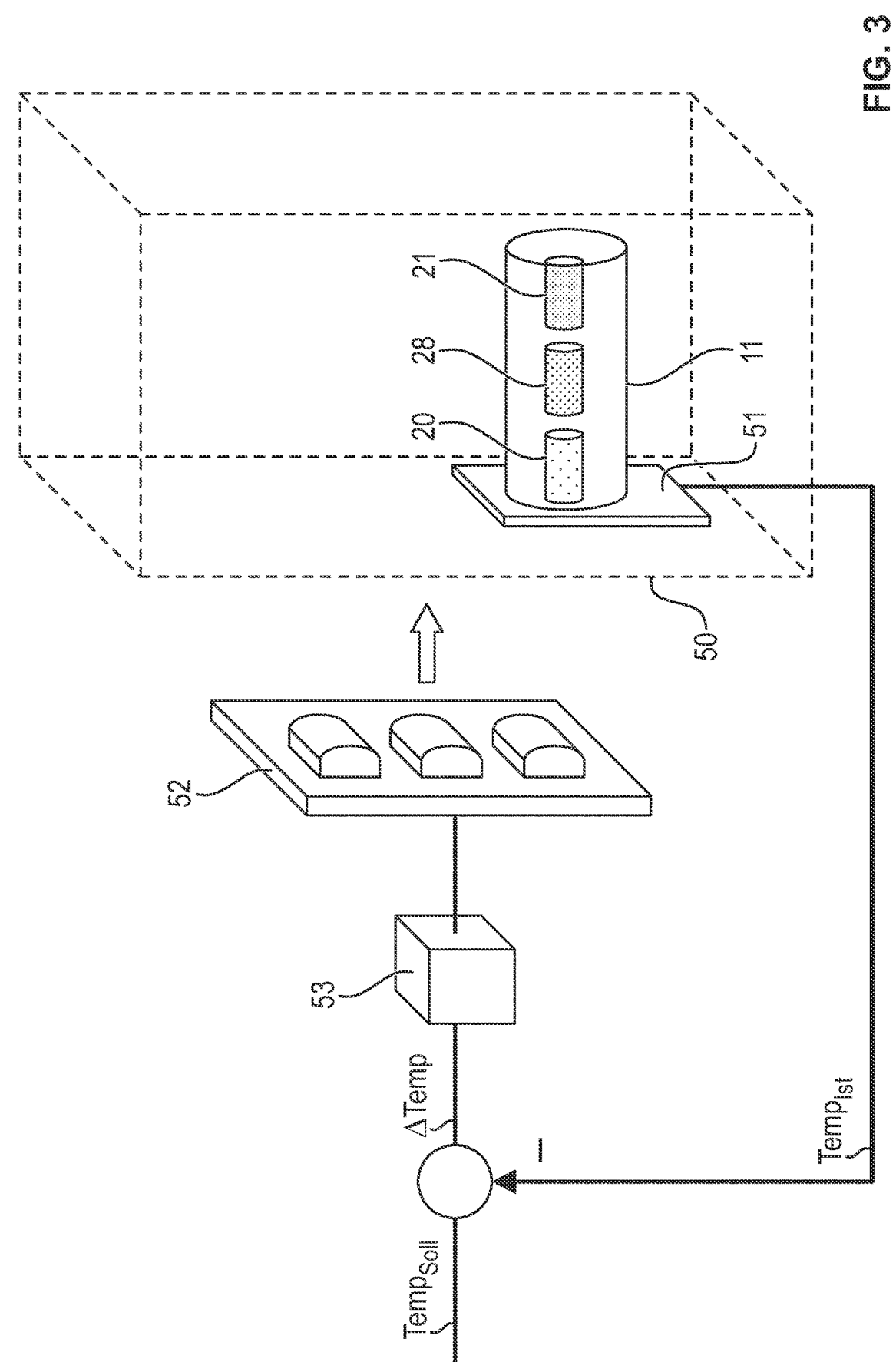
FIG. 3 is a schematic view showing a control loop according to the invention.

FIG. 3 schematically shows a control loop for controlling the temperature of the measuring electrode 20 of the sensor 10. In the example shown, the reference variable is a specified setpoint temperature $Temp_{Soll}$, wherein the measuring electrode 20 is to have a constant setpoint temperature $Temp_{Soll}$. The controlled variable is the measured actual temperature $Temp_{Ist}$ of the measuring electrode 20. The control deviation $Temp_{Soll}-Temp_{Ist}$ is denoted by $\Delta Temp$.

This control loop includes the following components:
a control system 50, which in the present case comprises the two electrodes 20 and 21 and the electrolyte 28, wherein the temperature of the measuring electrode 20 is to be controlled (maintained at a constant value $Temp_{Soll}$), a sensor 51 that measures the controlled variable $Temp_{Ist}$ and is described below, an actuator 52, in this case a heater which is able to increase the temperature of the electrode 20, which influences the controlled variable $Temp_{Ist}$, and a controller (signal-processing control unit) 53, which controls the actuator 52 depending on the control deviation $\Delta Temp$ determined.

Disturbance variables are in particular the ambient temperature and the temperature of the breath sample A and thus of the measuring chamber sample Pr. Chemical reactions in the sensor can also influence the temperature of the measuring electrode 20 and are a possible further disturbance variable.

The control gain for this control is that the control deviation $\Delta Temp$ should be brought to zero. Because the ambient temperature is usually less than or negligibly greater than the setpoint temperature $Temp_{Soll}$, unilateral control is often sufficient, in which the actuator 52 can increase the value of the controlled variable but not decrease it. However, if the sensor arrangement 100 is to be used at a high ambient temperature, it is also possible for the sensor arrangement 100 to have additional controllable cooling with the actuator 52 including a heater and a cooler (as part of a heating system and a cooling system).

Several embodiments for the sensor 51 and for the actuator 52 are described below. The sensor 51 measures the controlled variable at a measuring position on or in a measurement object. In the embodiment example, the measurement object is the measuring electrode 20 or the electrical contact 2 of the measuring electrode 20. The counter electrode 21 or the electrical contact 3 of the counter electrode 21 can also function as the measurement object. Because the measuring position is in or at the measurement object 20, 2, measurement of the controlled variable (the actual temperature $Temp_{Ist}$) is achieved with only a small error and only a very small delay (latency). If the temperature Temp of the measuring electrode 20 were measured at a measuring position outside the electrochemical sensor 10, the measured temperature at this spatially distant measuring position may deviate in a relevant way from the actual temperature $Temp_{Ist}$ of the measuring electrode 20 at the time of measurement.

Figure 4:
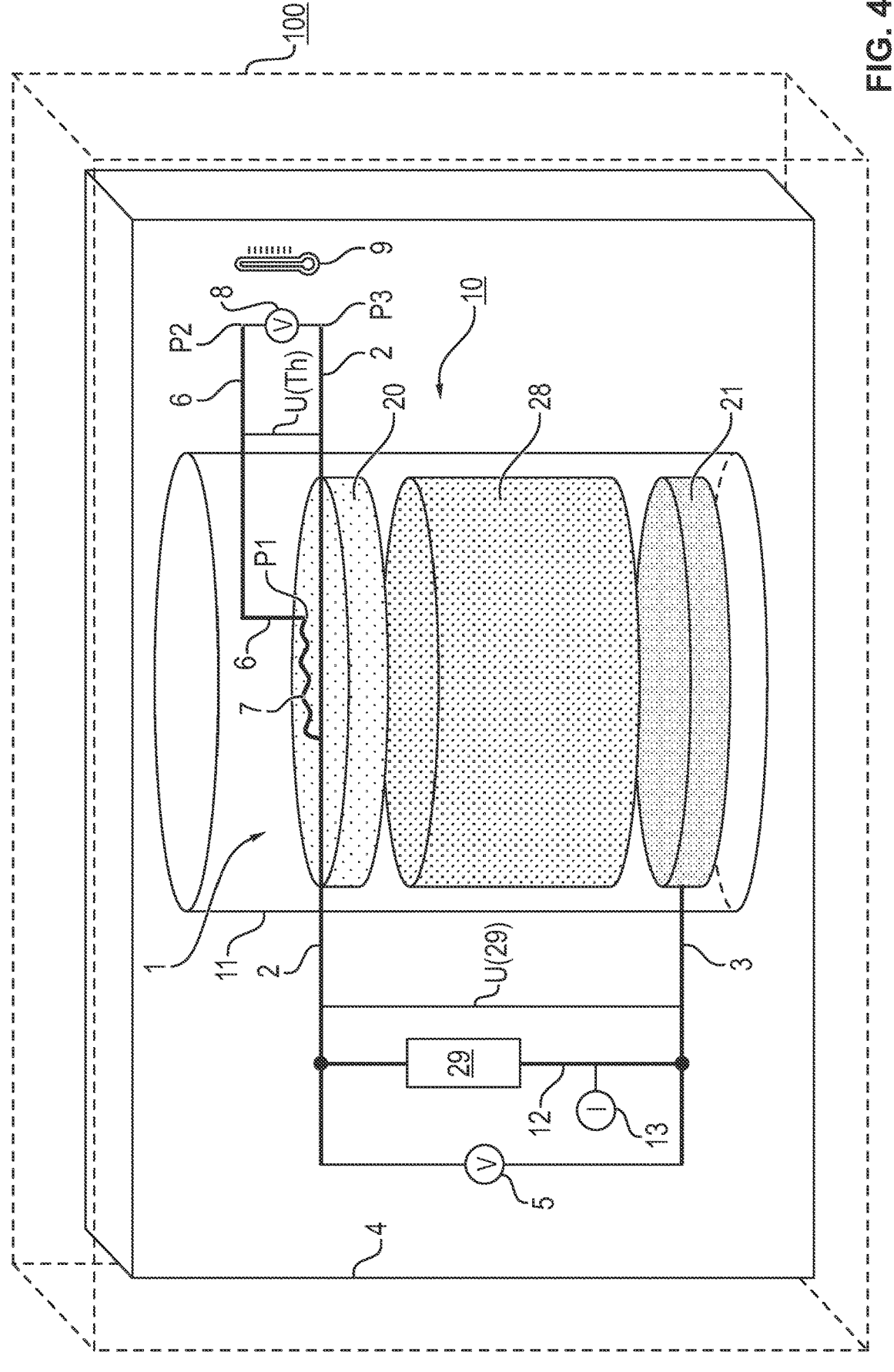
FIG. 4 is a schematic view showing an embodiment of the sensor assembly and illustrating how the temperature of the measuring electrode is measured using a thermocouple with a contact segment on the measuring electrode.
Figure 5:
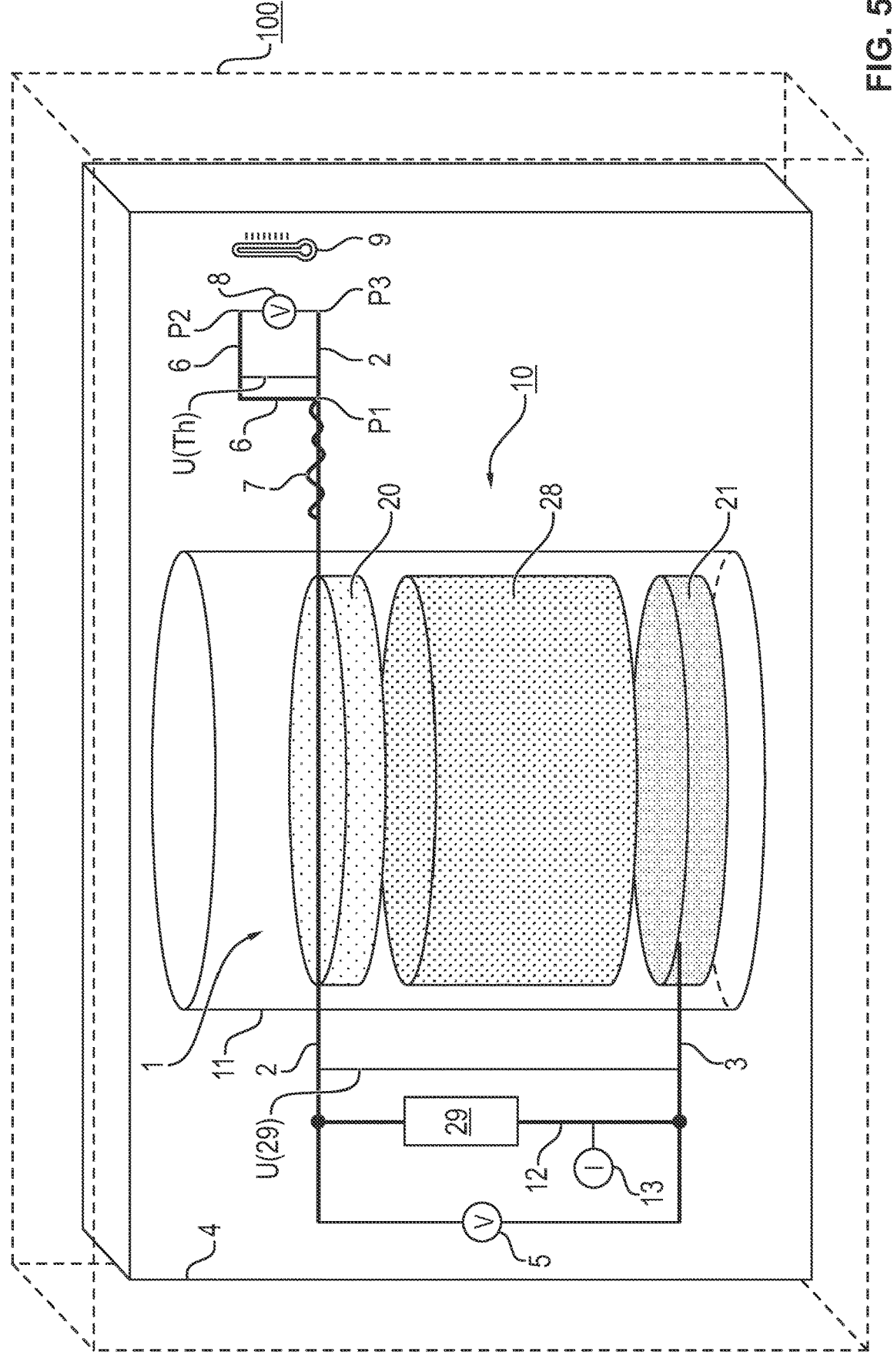
FIG. 5 is a schematic view showing a variation of the embodiment of FIG. 4 wherein the contact segment is arranged at the electrical contact of the measuring electrode.

FIG. 4 and FIG. 5 schematically show an embodiment of the temperature sensor 51 for controlling the electrode temperature. In addition, an exemplary embodiment of a region of the sensor arrangement 100 is shown. Between an end face of the measuring electrode 20 and an end face of the counter electrode 21 there is a membrane impregnated with the electrolyte 28. A good thermal contact is established between the two electrodes 20 and 21 thanks to the membrane 28. Therefore, the two electrodes 20 and 21 and the two electrical contacts 2 and 3 have approximately the same temperature in many cases. A schematically shown circuit board 4 is adjacent to the cylindrical measuring chamber 1.

A connecting wire 12 with a measuring resistor 29 is arranged between the two wires 2 and 3, which contact the measuring electrode 20 and the counter electrode 21, respectively. As already explained, oxidation of breath alcohol causes an electric current to flow through the connecting wire 12. This current causes a voltage drop U(29) at the measuring resistor 29. A voltage sensor 5 on the circuit board 4 measures the voltage drop U(29) across the measuring resistor 29. This voltage drop U(29) is a measure of the content of breath alcohol in the measuring chamber sample Pr, and thus the breath sample A. In this embodiment, the voltage drop U(29) is an additional detection variable.

In the embodiment according to FIG. 4 and FIG. 5 a thermocouple described below indirectly measures the coincident temperature of the two electrodes 20 and 21 and the two electrical contacts (platinum wires) 2 and 3. In many cases these temperatures differ from each other only by a negligible amount. This thermocouple exploits the Seebeck effect, which has already been described above. Exemplary realization forms of the thermocouple are described below.

In the realization forms according to FIG. 4 and FIG. 5 the electrical contact 2 for the measuring electrode 20 comprises a platinum wire. The measuring electrode 20 and the electrical contact 2 belong to conductor A. A measuring element with a different Seebeck coefficient belongs to conductor B. This measuring element comprises a contact segment 7 and a connection segment 6. The contact segment 7 is made, for example, of gold or platinum or iridium and is in a thermal contact and in an electrical contact with the measuring electrode 20. This contact between the contact segment 7 of the measuring electrode 20 is made, for example, in the form of a winding around the measuring electrode 20 or by spot welding. Thanks to the thermal contact, the contact segment 7 has approximately the same temperature than the measuring electrode 20. The connection segment 6 acts as a measuring wire that electrically and thermally connects the contact segment 7 to the circuit board 4.

The temperature Temp(P1) at a point P1 is sought. This temperature Temp(P1) in the point P1 agrees sufficiently exactly with the sought temperature of the measuring electrode 20. In the embodiment according to FIG. 4, the point P1 belongs to the area in which the contact segment 7 contacts the measuring electrode 20. In the shown implementation the contact segment 7 is connected with the connection segment 6 in the point P1. Preferably, a distance occurs between the point P1 and the area in which the electrical contact 2 contacts the measuring electrode 20.

The above-mentioned conductor A (measuring electrode 20 and electrical contact 2) connects the point P1 on the measuring electrode 20 with the point P3 on the circuit board 4. The conductor B (connection segment 6) connects the point P1 with the point P2 on the circuit board 4, cf. FIG. 4 and FIG. 5. Preferably, the connection segment has the same Seebeck coefficient k(B) throughout its length. In one implementation even the entire measuring element 6, 7 has the same Seebeck coefficient throughout its length. This is preferably achieved by the two segments 6 and 7 being made of the same electrically conductive material. It is also possible to use a Seebeck coefficient k(B) averaged over the length of the connecting segment 6 or of the measuring element 6, 7 for the temperature measurement.

The Seebeck coefficient k(B) of the connecting segment 6 differs from the Seebeck coefficient k(A) of the conductor A. The Seebeck coefficient k(A) depends on the Seebeck coefficient of the electrical contact 2 and optionally on that of the measuring electrode 20. Both Seebeck coefficients k(A) and k(B) are known by the design of the sensor arrangement 100. Furthermore, the assumption is used that the Seebeck coefficients k(A) and k(B)—or at least the difference k(A)–k(B) between them—remain constant throughout the temperature range in which the sensor arrangement 100 is used.

It is also possible that the contact segment 7 does not contact the measuring electrode 20, but is spaced from the measuring electrode 20 and contacts the electrical contact 2. For example, the contact segment 7 is wrapped or twisted around the electrical contact 2. This embodiment variation is shown in FIG. 5. The point P1 is located in the area where the contact segment 7 makes contact with the electrical contact 2. Preferably, the point P1 is located at the connection between the contact segment 7 and the connection segment 6.

It is also possible that the connection segment 6 contacts the measuring electrode 20 or the electrical contact 2 in only one point P1. In this case, this idealized point-shaped contact area functions as the contact segment. The Seebeck coefficient k(A) is then preferably equal to the Seebeck coefficient of the measuring electrode 20 or the electrical contact 2, resp.

The connection segment (the measuring wire 6) and the electrical contact 2 are connected to the circuit board 4. The connection point between the electrical contact 2 and the PCB 4 functions as the point P2, and the connection point between the connection segment 6 and the PCB 4 functions as the point P3. A reference temperature sensor 9 on the circuit board 4 measures the temperature Temp(P2), i.e. the temperature of the electrical contact 2 at the point P2, which corresponds sufficiently accurately to the temperature of the connection segment 6 at the point P3. It is also possible that the reference temperature sensor 9 measures the temperature of the connection segment 6 at point P3. The reference temperature sensor 9 is configured, for example, as an NTC thermistor (NTC=Negative Temperature Coefficient).

A voltage sensor 8 measures an indicator of the electrical voltage between points P2 and P3 on board 4. This measured voltage acts as the thermoelectric voltage (thermo voltage) U(Th). The only unknown is the temperature Temp(P1) at the measurement position P1 near the electrode.

The thermocouple of the embodiment according to FIG. 4 and FIG. 5 includes the connection segment 6, the contact segment 7 and the sensors 8 and 9. The electrical contact 2 further assume a function of the thermocouple.

In the example shown in FIG. 4 and FIG. 5, a thermocouple (thermoelement) is used which measures the temperature Temp(P1) of the measuring electrode 20. In many cases it can be assumed with sufficient accuracy that the counter electrode 21 always has the same temperature as the measuring electrode 20. It is also possible to provide a further thermocouple which measures the temperature of the counter electrode 21 and is preferably constructed in exactly the same way as the one thermocouple in FIG. 4.

An advantage of the embodiments according to FIG. 4 and FIG. 5 is that neither the contact segment 7 nor the connection segment 6 necessarily need to be electrically insulated from the measuring electrode 20. As a rule, no appreciable current flows through the connection segment 6. The measuring element 6, 7 is preferably made of a metal which is chemically resistant to the electrolyte 28.

Figure 6:
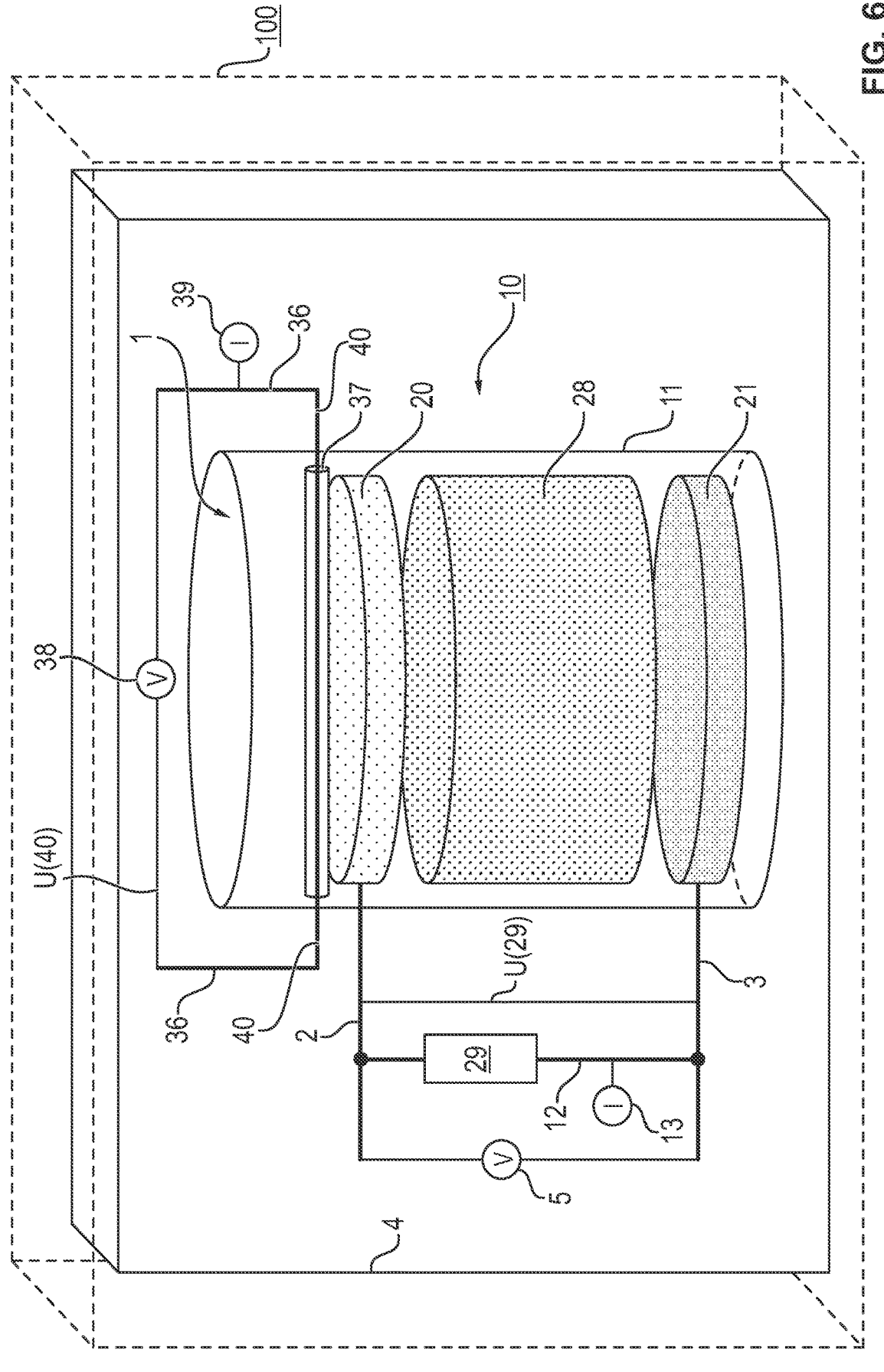
FIG. 6 is a schematic view showing an embodiment of the sensor assembly and illustrating how to measure the temperature of the measuring electrode using a straight measuring wire at one end face.

FIG. 6 shows another embodiment of the sensor 51 for the controlled variable, where in the example shown the temperature of the measuring electrode 20 is the controlled variable.

A contact segment 40 in the form of a wire is in thermal contact with one end face of the measuring electrode 20. In the implementation form shown, this is the end face facing the measuring chamber 1. It is also possible that the other end face is in thermal contact with the contact segment 40. Electrical insulation 37 electrically insulates the contact segment 40 from the measuring electrode 20. It is possible, but in many cases not necessary thanks to the electrical insulation 37, that the material of the contact segment 40 is chemically resistant to the electrolyte 28. However, a chemically resistant contact segment 40 will not be attacked by the electrolyte 28 even if the electrical insulation 37 has a defect (leak). The electrical insulation 37 has a sufficiently high thermal conductivity and preferably comprises an insulating sheath around the contact segment 40, for example made of thin-walled polytetrafluoroethylene (PTFE). The electrical insulation 37 is also chemically resistant to the electrolyte 28 and does not alter the electrolyte 28.

The contact segment 40 is in the form of a wire which is passed through the electrical insulation 37. At both ends, this contact segment 40 is contacted by a respective connection segment 36. The connection segments 36 connect the two ends of the contact segment 40 to a voltage sensor 38. The two segments 40, 36 are components of an electrical circuit through which a current flows. Preferably, this electrical circuit is in electrical connection with a voltage supply unit of the analyzer. This voltage supply unit is not shown in the figures.

Thanks to the thermal contact, the temperature of the contact segment 40 coincides sufficiently precisely with the temperature of the measuring electrode 20. Also the connection segments 36 have the same temperature as the contact segment 40 and thus as the measuring electrode 20. As is known, the electrical resistance of an electrically conductive material depends on the temperature of the material, usually in such a way that the greater the temperature, the greater the electrical resistance (positive temperature coefficient). At every temperature which occurs during a practical use the connection segments 36, the connection segments 36 have a lower electrical resistance than the contact segment 40. Due to these two reasons, the electrical resistance of the contact segment 40 or even of the whole measuring element 40, 36 is an indicator for the temperature of the measuring electrode 20.

The voltage sensor 38 measures an indicator of the voltage drop U(40) between the two ends of the contact segment 40. Because the contact segment 40 is electrically conductive, this voltage drop U(40) correlates with the temperature Temp(P1) of the contact segment 40. A current (amperage) sensor 39 measures the magnitude I of the current flowing through the circuit containing the contact segment 40 and the connection segments 36. It is possible that the magnitude I of the current flowing through this circuit is controlled with the control gain that the current magnitude should remain constant. In many cases, the sought temperature of the measuring electrode 20 is then with sufficient reliability proportional to the voltage drop U(40). It is also possible to keep the voltage drop U(40) constant by control. In this case, the current I is sufficiently proportional to the desired temperature Temp(P1).

Figure 7:
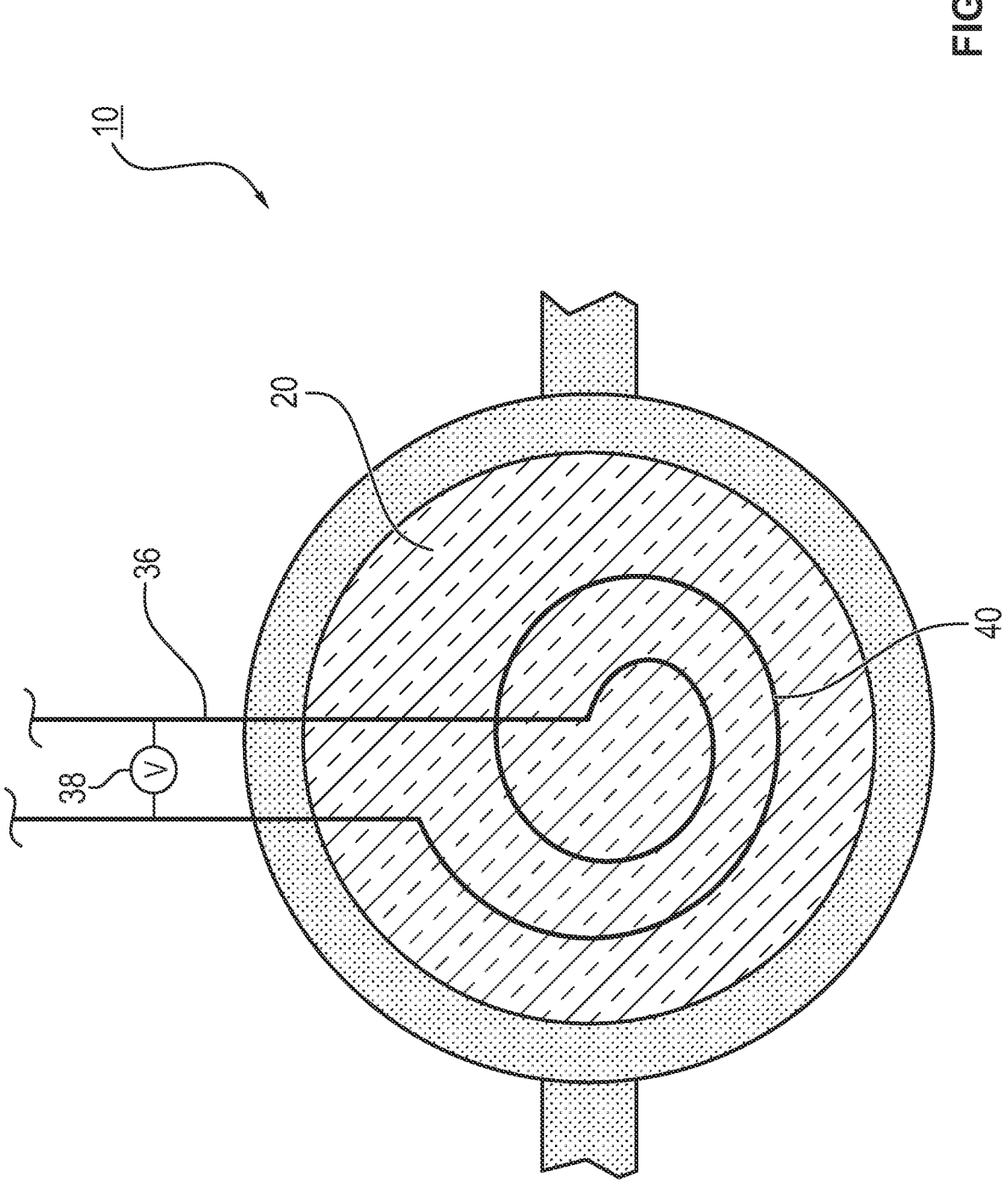
FIG. 7 is a schematic sectional view illustrating how the temperature of the measuring electrode is measured by means of a wound measuring wire at the end face.

FIG. 7 shows a preferred embodiment of the measuring element 40, 36. The center axis of the cylindrical, in particular disk-shaped, measuring electrode 20 is perpendicular to the drawing plane of FIG. 7. FIG. 7 shows how the contact segment 40 is in thermal contact with an end face of the measuring electrode 20. In order to extend the distance of that section of the contact segment 40 which is in thermal contact with the measuring electrode 20, the contact segment 40 preferably has several windings. In FIG. 7 the electrical insulation 37 is not shown.

FIG. 4 to FIG. 7 show different configurations for measuring the current temperature of an electrode 20, 21. It is possible to combine two configurations. In particular, it is possible that the contact segment 40 is in thermal contact with an end face as well as in thermal contact with the outer surface of the electrode 20, 21.

The following description refers to the measuring electrode 20 as the electrode whose temperature is measured. In an alternative embodiment, the actual temperature of the counter electrode 21 is measured instead or additionally, for example also by one of the embodiments according to FIG. 4 to FIG. 7.

Ideally, the measuring electrode 20 and the counter electrode 21 always have the same temperature, but in practice they usually differ from each other. If the temperature of the measuring electrode 20 differs from the temperature of the counter electrode 21 by more than a predetermined threshold, a signal-processing evaluation unit (such as a processor and memory unit that is mounted on circuit board 4) of the sensor arrangement 100 preferably detects this event and, particularly preferably, generates a message. This message is output in a form that can be perceived by a human.

In many cases, when the temperature difference is above the threshold, it is not possible for the sensor 10 to reliably measure the content of breath alcohol in a breath sample Ap. It is possible to use the sensor arrangement 100 again for a measurement only when the difference between the two electrode temperatures has become smaller and is below the threshold. In another embodiment, the measured temperature of the counter electrode 21 is used to correct a measurement result of the measuring electrode 20 by calculation.

The control unit shown in FIG. 3 includes an actuator 52 in the form of a heater which is capable of heating at least the measuring electrode 20. Because the counter electrode 21 is in good thermal contact with the measuring electrode 20, the heater 52 generally also heats the counter electrode 21. Two preferred embodiments of this heater 52 are described below.

Figure 8:
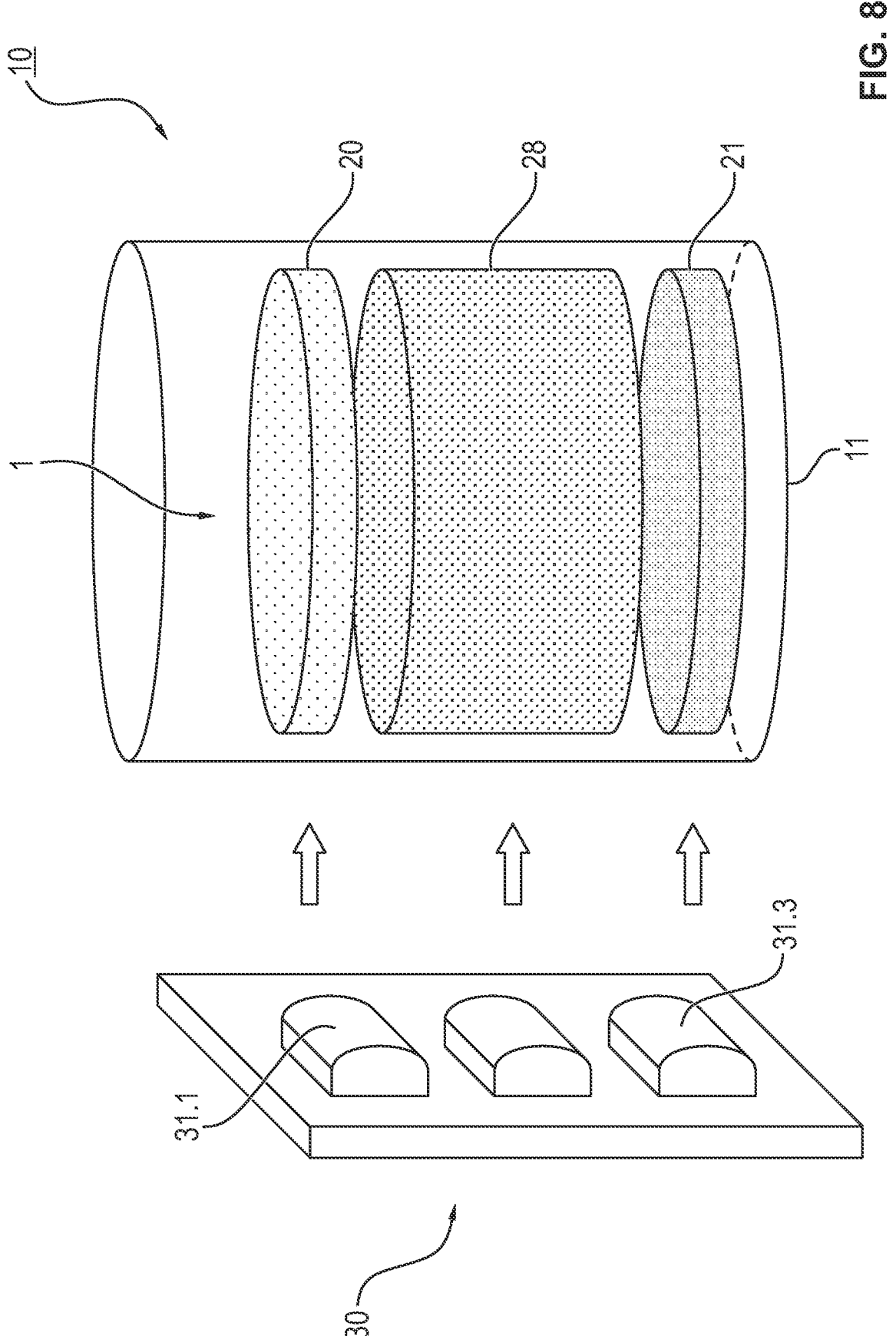
FIG. 8 is a schematic view illustrating how the measuring electrode is heated with an array of LEDs.

In the embodiment according to FIG. 8 the heater 52 comprises a radiation source in the form of an LED arrangement 30 with at least one LED, preferably several LEDs. Three LEDs 31.1 to 31.3 are shown by way of example. A different number is also possible. Each LED 31.1 to 31.3 emits electromagnetic radiation. The measuring electrode 20 and also the counter electrode 21 are preferably made of a dark material and therefore absorb a considerable part of the incident electromagnetic radiation. As a result, the measuring electrode 20 and also the counter electrode 21 heat up.

This embodiment makes it possible to heat up the measuring electrode 20 and the counter electrode 21 without contact. The LEDs 31.1 to 31.3 can be switched on and off again with virtually no time delay, and when the LEDs 31.1 to 31.3 are switched on, the measuring electrode 20 and the counter electrode 21 heat up rapidly.

In one embodiment, all LEDs 31.1 to 31.3 or only at least a subset of the LEDs can be optionally switched on. This makes it possible to emit at least two different amounts of thermal energy and thereby selectively heat the measuring electrode 20 by a larger or smaller amount or faster or slower. In the case of a large control deviation ΔTemp, all LEDs 31.1 to 31.3 are preferably switched on, and in the case of a small control deviation ΔTemp, only a subset of the LEDs are switched on. It is also possible to vary the electrical voltage applied to the LEDs or the strength of the electrical current flowing through the LEDs. This changes the absorbed electrical power and thus also the emitted radiant power.

In a further embodiment, the LEDs 31.1 to 31.3 are operated in pulsed mode. By means of a pulse width modulation, the actually emitted amount of heat is adapted to a desired amount of heat to be emitted. The higher the pulse frequency at a constant pulse duration is or the higher the pulse duration at a constant pulse frequency is, the higher the amount of heat is emitted. It is also possible to increase the duration of a pulse to increase the amount of heat emitted. The pulse frequency is set so that the thermal time constants of the electrodes 20, 21 are longer than the pulse frequency. This is possible because the LEDs 31.1 to 31.3 have a low thermal mass and can also be turned on and off quickly. The embodiment with the pulse width modulation can be combined with the embodiment that all or only a part of the LEDs 31.1 to 31.3 can optionally be switched on and off. However, the embodiment with the pulse width modulation also makes it possible to adjust the amount of emitted thermal energy and to always switch on and off all LEDs 31.1 to 31.3.

In a preferred embodiment, the LED arrangement 30 is mounted outside the housing 11, for example on the outside of a housing of the analyzer. This embodiment makes it easier to replace a defective LED 31.1 to 31.3 or even the entire LED arrangement 30. The LED arrangement 30 may be configured as described in DE 10 2019 003 021 A1 (DE 10 2019 003 021 A1 is hereby incorporated by reference).

Preferably, each LED 31.1 to 31.3 emits radiation in a wavelength range between 400 and 500 nm. Wavelengths in this range pass through many types of plastic without the plastic absorbing a significant portion of the transmitted radiation, particularly when the plastic is of a light color or is approximately transparent so that electromagnetic radiation transmits through the plastic without significant absorption. Preferably, the housing of the analyzer with the sensor arrangement 100 is made of such a plastic that is transparent to electromagnetic radiation. Preferably, the maximum rated power of the LED arrangement 30 is between 5 W and 7 W. This embodiment is sufficient to heat the measuring electrode 20 and the counter electrode 21 sufficiently quickly and sufficiently strongly, and yet consumes relatively little electrical energy.

In an alternative embodiment, the measuring electrode 20, optionally also the counter electrode 21, is heated by a heating wire. This heating wire is in thermal contact with the electrode 20, 21 to be heated and is electrically insulated from this electrode 20, 21. Particularly preferably, the measuring element 40, 36 is connected to the contact segment 40 of FIG. 6 and/or FIG. 7 is additionally used as a heating wire. This embodiment saves an additional heating wire. The heating wire/measuring element 40, 36 is heated to heat the measuring electrode 20, and furthermore, as described above with reference to FIG. 6 the electrical resistance of the heating wire/contact segment 40 is measured and acts as a measure of the temperature of the measuring electrode 20. Because the voltage U(40) applied to the contact segment 40 and/or the current I of the current flowing through the circuit with the contact segment 40 is measured, it is possible to control the temperature $\text{Temp}_{Ist}$ of the measuring electrode 20 using the contact segment 40.

In one embodiment, the heating wire/contact segment 40 is printed on a plastic film. In many cases, this embodiment allows the heating wire/contact segment 40 to be manufactured quickly and automatically.

While specific embodiments of the invention have been shown and described in detail to illustrate the application of the principles of the invention, it will be understood that the invention may be embodied otherwise without departing from such principles.

| List of reference characters | |
|---|---|
| 1 | Measuring chamber, receives the measuring chamber sample Pr, surrounds the electrochemical sensor 10 |
| 2 | Contact wire made of platinum or gold, electrically contacts the measuring electrode 20 |
| 3 | Contact wire made of platinum or gold, electrically contacts the counter electrode 21 |
| 4 | Circuit board on which voltage sensors 5 and 6 are mounted |
| 5 | Voltage sensor, measures the voltage drop U(29) at the measuring resistor 29 |
| 6 | Connection segment made of gold or platinum, connects contact segment 7 with point P2 on board 4 |
| 7 | Contact segment made of gold or platinum, is in a thermal and optionally additionally in an electrical contact with the measuring electrode 20 or the electrical contact 2 |
| 8 | Voltage sensor, measures the voltage that occurs between the two wires 2 and 6 due to the Seebeck effect |
| 9 | Reference temperature sensor, measures an indicator of the temperature of the wire 6 at a reference position on the board 4 |
| 10 | Electrochemical sensor in the measuring chamber 1, comprises the electrodes 20, 21, the electrical contacts 2 and 3 and the electrolyte 28 |
| 11 | Sensor housing of electrochemical sensor 10 |
| 12 | Connecting wire between contact wires 2 and 3 |
| 13 | Current (amperage) sensor, measures the intensity of the current flowing through the connection wire 12 |

-continued

| List of reference characters | |
|---|---|
| 20 | Measuring electrode of the sensor 10, preferably made of platinum or gold |
| 21 | Counter electrode of the sensor 10, preferably made of platinum or gold |
| 28 | Electrolyte (sulfuric acid) inside the measuring chamber 1, arranged between the electrodes 20 and 21 |
| 29 | Electrical measuring resistance between the two electrodes 20, 21 |
| 30 | LED array with LEDs 31.1, . . . , acts as a radiation source and thus as a heater |
| 31.1, . . . | LEDs of the LED array 30, emit electromagnetic radiation toward the electrodes 20, 21 to |
| 36 | Connection segments, connect the two ends of the contact segment 40 to the voltage sensor 38 |
| 37 | electrical insulation around the contact segment 40 |
| 38 | Voltage sensor, measures the voltage drop U(40) between the two ends of the contact segment 40 |
| 39 | Current (amperage) sensor, measures the intensity I of the current flowing through the measuring element 40, 36 |
| 40 | Contact segment, is in thermal contact with an end face of the measuring electrode 20, electrically insulated from the measuring electrode 20 by the insulation 37, connected at its two ends to the two connection segments 36, in one embodiment additionally functions as a heating element |
| 50 | Control system that controls electrode temperature, includes electrodes 20, 21 and sensor 51 |
| 51 | Temperature sensor that measures the controlled variable (actual temperature of electrodes 20, 21) |
| 52 | Actuator (electrode heater and/or cooler), which changes the controlled variable |
| 53 | Controller (signal-processing control unit), which controls the actuator 52 |
| 100 | Sensor arrangement according to the invention, comprises the electrochemical sensor 10, the temperature sensor, the heating, the optional cooling, and the control unit 53, belongs to an analysis device (analyzer) |
| A | Electrical conductor from point P1 to point P3 |
| Ap | Breath sample delivered by the subject, the measuring chamber sample Pr is included in the breath sample |
| B | Electrical conductor from point P1 to point P2 |
| Ö.a | Outlet-side opening in the housing 11, through which the measuring chamber sample Pr flows out of the measuring chamber 1 |
| Ö.e | Opening on the inlet side in the housing 11, through which the measuring chamber sample Pr flows into the measuring chamber 1 |
| P1 | Point of the contact segment 7, 40, where the two conductors A and B begin |
| P2, P3 | Points on the board 4, the thermoelectric voltage U(Th) occurring between these points |
| Pr | Measuring chamber sample, which is that part of the breath sample A emitted by the subject that enters measuring chamber 1, ideally comes from the subject's lungs, is analyzed for breath alcohol |
| ΔTemp | Control deviation of control system 50, equal to $Temp_{Soll} - Temp_{Ist}$ |
| $Temp_{Soll}$ | Predetermined set point temperature of control system 50 |
| $Temp_{Ist}$ | Measured actual temperature of the control system 50 |
| U(29) | Voltage drop across measuring resistor 29, measured by voltage sensor 5 |
| U(40) | Voltage drop between the two ends of the contact segment 40, measured by the voltage sensor 38 |
| U(Th) | Thermal voltage between wires 2 and 6 on board 4 and thus between points P2 and P3, measured by voltage sensor 8 |

What is claimed is:

1. A sensor arrangement for analyzing a gas for a predetermined gas component, the sensor arrangement comprising:

an electrochemical sensor, the electrochemical sensor comprising: a measuring electrode, a counter electrode, an electrical contact for the measuring electrode, an electrical contact for the counter electrode, and an electrolyte between the measuring electrode and the counter electrode; and a temperature sensor unit, the temperature sensor unit comprising a temperature sensor, an electrically conductive measuring element, and a voltage sensor, the electrically conductive measuring element comprising a contact segment that is in planar contact with a measurement object of the electrochemical sensor such that thermal contact is established between the contact segment and the measurement object, and a connection segment electrically and/or thermally connecting the contact segment to the temperature sensor;

wherein the contact segment is electrically conductively connected to the measurement object, wherein the measurement object is one element of the group consisting of the measuring electrode, the counter electrode, the electrical contact for the measuring electrode, or the electrical contact for the counter electrode, wherein the sensor arrangement is configured to measure a detection variable of the electrochemical sensor, wherein the measurable detection variable correlates with a presence and/or concentration of the gas component, wherein the temperature sensor is configured to measure at a measuring position a variable that correlates with the temperature of the contact segment, wherein the measuring position is spatially distanced from each of the measuring electrode, the counter electrode, the electrical contact for the measuring electrode, and the electrical contact for the counter electrode;

wherein the temperature sensor unit is configured to determine an indication of the temperature of the measuring electrode and/or an indication of the temperature of the counter electrode depending on the measured variable correlating with the contact segment temperature, wherein the connection segment has a Seebeck coefficient that is different than a Seebeck coefficient of the measurement object, wherein the voltage sensor is configured to provide an indicator of a thermoelectric voltage, the thermoelectric voltage occurring between the connection segment and the measurement object or the electrical contact for the measurement object, wherein the temperature sensor is configured to measure the variable that correlates with the temperature of the contact segment by measuring at the measuring position a variable that correlates with the temperature of the connection segment, and wherein the temperature sensor unit is configured to determine the temperature of the measurement object based on the measured thermoelectric voltage and the measured variable correlating with the temperature of the connection segment.

2. A sensor arrangement according to claim 1, wherein:
the measurement object is the measuring electrode or the counter electrode;
the connection segment has a Seebeck coefficient that is different than a Seebeck coefficient of the electrical contact of the measurement object; and
the voltage sensor is configured to measure an indicator of a thermoelectric voltage occurring between the connection segment and the electrical contact of the measurement object.

3. A sensor arrangement according to claim 2, wherein the temperature sensor is configured to measure the temperature of the electrical contact of the measurement object or measure a variable which correlates with the temperature of the electrical contact of the measurement object.

4. A sensor arrangement according to claim 1, wherein:
the contact segment has electrical insulation which electrically insulates the contact segment from the measurement object;
the measuring element is configured such that the contact segment has the same temperature as the measurement object, the same temperature is achieved via the thermal contact between the contact segment and the measurement object; and
the temperature sensor is configured to measure as the variable that correlates with the temperature of the contact segment a variable that correlates with the temperature of the connection segment.

5. A sensor arrangement according to claim 4, wherein the temperature sensor is configured to measure an indicator of the electrical resistance of the connection segment, as the variable correlating with the temperature of the connection segment.

6. A sensor arrangement according to claim 1, further comprising:
a controllable heater; and
a signal processing control unit,
wherein the heater is configured to heat the measuring electrode and/or the counter electrode, wherein the control unit is configured to control by closed-loop control an actual temperature of the measuring electrode and/or to control an actual temperature of the counter electrode with a control gain that the controlled temperature maintains within a predetermined temperature range; and wherein the control unit is configured to control the actual temperature by controlling the heater depending on a signal from the temperature sensor unit.

7. A sensor arrangement according to claim 6, wherein:
the heater comprises a controllable radiation source;
wherein the radiation source is configured to emit electromagnetic radiation toward the measuring electrode and/or the counter electrode; and
wherein the control unit is configured to cause an intensity and/or energy of the emitted radiation to be set to a value, the value setting depending on a signal from the temperature sensor unit.

8. A sensor arrangement according to claim 6, wherein:
the measurement object is the measuring electrode or the counter electrode; and
the heater comprises an electrically conductive heating element;
wherein the electrically conductive heating element comprises the contact segment.

9. A sensor arrangement according to claim 8, wherein the temperature sensor is configured to measure an indicator of the electrical resistance of the electrically conductive heating element as the variable correlating with the temperature of the contact segment.

10. A sensor arrangement according to claim 6, wherein:
the control unit is configured to calculate a setpoint value for electrical voltage to be applied to the heater, the calculation is performed as a function of a signal from the temperature sensor unit; and
the sensor arrangement is configured to adjust the electrical voltage actually applied to the heater to the setpoint.

11. A sensor arrangement according to claim 6, further comprising a controllable cooling system, wherein:
the cooling system is configured to cool the measuring electrode and/or the counter electrode; and
the control unit is configured to control the cooling system for control of the temperature depending on a signal from the temperature sensor unit.

12. A process for analyzing a gas for a predetermined gas component, the process comprising the steps of:
providing a sensor arrangement, the sensor arrangement comprising an electrochemical sensor comprising a measuring electrode, a counter electrode, an electrical contact for the measuring electrode, an electrical contact for the counter electrode, and an electrolyte between the measuring electrode and the counter electrode, the sensor arrangement further comprising a temperature sensor unit, the temperature sensor unit comprising a temperature sensor, an electrically conductive measuring element, and a voltage sensor, the measuring element comprising a contact segment and a connection segment, wherein the contact segment is in planar contact with a measurement object of the electrochemical sensor such that thermal contact is established between the contact segment and the measurement object, wherein the contact segment is electrically conductively connected to the measurement object, wherein the measurement object is one element of the group consisting of the measuring electrode, the counter electrode, the electrical contact for the measuring electrode or the electrical contact for the counter electrode, wherein the connection segment electrically and/or thermally connects the contact segment to the temperature sensor, the connection segment having a Seebeck coefficient that is different than a Seebeck coefficient of the measurement object, the voltage sensor being configured to provide an indicator of a thermoelectric voltage, the thermoelectric voltage occurring between the connection segment and the measurement object or the electrical contact for the measurement object;

measuring a detection variable, wherein the measured detection variable correlates with a presence of the gas component and/or concentration of the gas component;

with the temperature sensor, measuring at a measuring position a variable that correlates with the temperature of the contact segment by measuring at the measuring position a variable that correlates with the temperature of the connection segment;

wherein the measuring position is spatially distanced from each of the measuring electrode, the counter electrode, the electrical contact for the measuring electrode, and the electrical contact for the counter electrode; and with the temperature sensor unit, determining the temperature of the measurement object based on the measured thermoelectric voltage and the measured variable correlating with the temperature of the connection segment.

13. A process according to claim 12, wherein:

the sensor arrangement further comprises: a controllable heater; and a signal processing control unit;

the process additionally comprises controlling, with the control unit, by closed-loop control an actual temperature of the measuring electrode and/or of the counter electrode with a control gain to maintain the actual temperature within a predetermined temperature range wherein when the determined actual temperature is below the temperature range, the control unit activates the heater to heat the measuring electrode and/or the counter electrode and subsequently deactivates the heater.

14. A sensor arrangement for analyzing a gas for a gas component, the sensor arrangement comprising:

an electrochemical sensor, the electrochemical sensor comprising: a measuring electrode, a counter electrode, an electrical contact for the measuring electrode, an electrical contact for the counter electrode, and an electrolyte between the measuring electrode and the counter electrode; and a temperature sensor unit, the temperature sensor unit comprising a temperature sensor, an electrically conductive measuring element, and a voltage sensor, the electrically conductive measuring element comprising a contact segment in planar contact with a measurement object of the electrochemical sensor such that thermal contact is established between the contact segment and the measurement object, and a connection segment electrically and/or thermally connecting the contact segment to the temperature sensor;

wherein the contact segment is electrically conductively connected to the measurement object, wherein the measurement object is one element of the group consisting of the measuring electrode, the counter electrode, the electrical contact for the measuring electrode, and the electrical contact for the counter electrode, wherein the sensor arrangement is configured to measure a detection variable of the electrochemical sensor, wherein the measurable detection variable correlates with a presence and/or concentration of the gas component, wherein the temperature sensor is configured to measure at a measuring position a variable that correlates with the temperature of the contact segment, wherein the measuring position is located at a spaced location from each of the measuring electrode, the counter electrode, the electrical contact for the measuring electrode, and the electrical contact for the counter electrode;

wherein the temperature sensor unit is configured to determine an indication of the temperature of the measuring electrode and/or an indication of the temperature of the counter electrode depending on the measured variable correlating with the contact segment temperature, wherein the connection segment has a connection segment Seebeck coefficient, wherein the measurement object has a measurement object Seebeck coefficient, wherein the connection segment Seebeck coefficient is not equal to the measurement object Seebeck coefficient, wherein the voltage sensor is configured to provide an indicator of a thermoelectric voltage, the thermoelectric voltage occurring between the connection segment and the measurement object or the electrical contact for the measurement object, wherein the temperature sensor is configured to measure the variable that correlates with the temperature of the contact segment by measuring at the measuring position a variable that correlates with the temperature of the connection segment, and wherein the temperature sensor unit is configured to determine the temperature of the measurement object based on the measured thermoelectric voltage and the measured variable correlating with the temperature of the connection segment.

* * * * *